(12) United States Patent
Hubbell et al.

(10) Patent No.: US 10,711,106 B2
(45) Date of Patent: Jul. 14, 2020

(54) HIGH ASPECT RATIO NANOFIBRIL MATERIALS

(71) Applicant: The University of Chicago, Chicago, IL (US)

(72) Inventors: Jeffrey A. Hubbell, Préverenges (CH); Carrie E. Brubaker, Lausanne (CH); Diana Velluto, London (GB)

(73) Assignee: The University of Chicago, Chicago, IL (US)

( * ) Notice: Subject to any disclaimer, the term of this patent is extended or adjusted under 35 U.S.C. 154(b) by 112 days.

(21) Appl. No.: 14/907,370

(22) PCT Filed: Jul. 24, 2014

(86) PCT No.: PCT/US2014/048009
§ 371 (c)(1),
(2) Date: Jan. 25, 2016

(87) PCT Pub. No.: WO2015/013510
PCT Pub. Date: Jan. 29, 2015

(65) Prior Publication Data
US 2016/0177036 A1    Jun. 23, 2016

Related U.S. Application Data

(60) Provisional application No. 61/858,314, filed on Jul. 25, 2013.

(51) Int. Cl.
| | | |
|---|---|---|
| *A61K 47/34* | (2017.01) | |
| *C08G 75/08* | (2006.01) | |
| *C08L 81/02* | (2006.01) | |
| *C08L 71/02* | (2006.01) | |
| *C08G 75/14* | (2006.01) | |
| *C08G 65/334* | (2006.01) | |
| *A61K 47/60* | (2017.01) | |

(52) U.S. Cl.
CPC .............. *C08G 75/08* (2013.01); *A61K 47/34* (2013.01); *A61K 47/60* (2017.08); *C08G 65/334* (2013.01); *C08G 75/14* (2013.01); *C08L 71/02* (2013.01); *C08L 81/02* (2013.01); *C08G 2650/30* (2013.01); *C08L 2203/02* (2013.01); *C08L 2205/04* (2013.01)

(58) Field of Classification Search
CPC ...... A61K 47/60; A61K 47/34; C08G 65/334; C08G 75/14; C08L 71/02
See application file for complete search history.

(56) References Cited

U.S. PATENT DOCUMENTS

| | | |
|---|---|---|
| 4,242,474 A | 12/1980 | Shinohara et al. |
| 4,292,400 A * | 9/1981 | Pollet ................. G03C 1/09 430/376 |
| 4,618,400 A | 10/1986 | Wood et al. |
| 4,732,938 A | 3/1988 | Grant et al. |
| 4,764,247 A | 8/1988 | Leveriza et al. |
| 4,795,660 A | 1/1989 | Cooray et al. |
| 4,923,924 A | 5/1990 | Grant et al. |
| 5,030,352 A | 7/1991 | Varady et al. |
| 5,268,305 A | 12/1993 | Ribi et al. |
| 5,294,690 A | 3/1994 | Iguchi et al. |
| 5,330,911 A | 7/1994 | Hubbell et al. |
| 5,374,668 A | 12/1994 | Kanemura et al. |
| 5,410,016 A | 4/1995 | Hubbell et al. |
| 5,427,915 A | 6/1995 | Ribi et al. |
| 5,446,090 A | 8/1995 | Harris |
| 5,502,102 A | 3/1996 | Nazareth |
| 5,529,914 A | 6/1996 | Hubbell et al. |
| 5,567,422 A | 10/1996 | Greenwald |
| 5,573,934 A | 11/1996 | Hubbell et al. |
| 5,575,815 A | 11/1996 | Slepian et al. |
| 5,612,390 A | 3/1997 | Iguchi et al. |
| 5,635,207 A | 6/1997 | Grinstaff et al. |
| 5,648,506 A | 7/1997 | Desai et al. |
| 5,688,855 A | 11/1997 | Stoy et al. |
| 5,702,717 A | 12/1997 | Cha et al. |

(Continued)

FOREIGN PATENT DOCUMENTS

| | | |
|---|---|---|
| EP | 1555278 A1 | 7/2005 |
| EP | 1 932 870 A1 | 6/2008 |

(Continued)

OTHER PUBLICATIONS

Aida et al., "Zinc N-substituted porphyrins as novel initiators for the living and immortal polymerizations of episulfide," Macromolecules. 23(17):3887-92 (1990).
Baker, Biodegradable Systems. *Controlled Release of Biologically Active Agents*. John Wiley and Sons, 84-131 (1987).
Ballini et al., "Amberlyst A-27, an efficient heterogeneous catalyst for the michael reaction of nitroalkanes with beta-substituted alkene acceptors," J Org Chem. 61(9):3209-11 (1996).
Bearinger et al., "PPS-PEG block copolymers render hydrophobic surfaces protein and cell resistant," European Cells and Materials. 2(Suppl. 1):45 (2001).
Bell et al., "Transfection mediated by gemini surfactants: engineered escape from the endosomal compartment," J Am Chem Soc. 125(6):1551-8 (2003).
Benoit et al., "pH-responsive polymeric siRNA carriers sensitize multidrug resistant ovarian cancer cells to doxorubicin via knockdown of polo-like kinase 1," Mol Pharm. 7(2):442-55 (2010).

(Continued)

*Primary Examiner* — Alma Pipic
(74) *Attorney, Agent, or Firm* — Clark & Elbing LLP

(57) ABSTRACT

The present invention features linear and three-dimensional supramolecular materials self-assembled from block copolymers comprising oligo(ethylene sulfide) (OES). The block copolymers assemble into fibrils, micelles, or matrices. The fibrillar materials are sensitive to oxidation, which leads to decreased OES block hydrophobicity and crystallinity, and increased water solubility of the polymer constituents. Molecular loading options, coupled with oxidative sensitivity, allow implantable or injectable fibrillar suspensions or cross-linked three-dimensional matrices to demonstrate significant biomedical potential, especially in the context of extracellular and intracellular molecular delivery and applications related to infection and disease.

18 Claims, 16 Drawing Sheets

(56) References Cited

U.S. PATENT DOCUMENTS

| | | | |
|---|---|---|---|
| 5,733,711 A | 3/1998 | Juengling | |
| 5,752,974 A | 5/1998 | Rhee et al. | |
| 5,801,033 A | 9/1998 | Hubbell et al. | |
| 5,817,840 A | 10/1998 | Nicolaou et al. | |
| 5,821,343 A | 10/1998 | Keogh | |
| 5,852,182 A | 12/1998 | Cook et al. | |
| 5,858,746 A | 1/1999 | Hubbell et al. | |
| 5,863,650 A | 1/1999 | Healy et al. | |
| 5,871,653 A | 2/1999 | Ling | |
| 5,874,500 A | 2/1999 | Rhee et al. | |
| 5,880,131 A | 3/1999 | Greenwald et al. | |
| 5,897,955 A | 4/1999 | Drumheller | |
| 5,925,494 A | 7/1999 | Horn | |
| 5,932,462 A | 8/1999 | Harris et al. | |
| 5,945,457 A | 8/1999 | Plate et al. | |
| 5,965,588 A | 10/1999 | Vazquez et al. | |
| 6,180,141 B1 | 1/2001 | Lemercier et al. | |
| 6,190,834 B1 | 2/2001 | Narahara et al. | |
| 6,224,903 B1 | 5/2001 | Martin et al. | |
| 6,303,277 B1 | 10/2001 | Hieda et al. | |
| 6,306,165 B1 | 10/2001 | Patnaik et al. | |
| 6,358,557 B1 | 3/2002 | Wang et al. | |
| 6,562,398 B1 | 5/2003 | Braach-Maksvytis et al. | |
| 6,624,245 B2 | 9/2003 | Wallace et al. | |
| 6,887,332 B1 | 5/2005 | Kagan et al. | |
| 6,958,212 B1 | 10/2005 | Hubbell et al. | |
| 7,056,704 B2 | 6/2006 | Tuschl et al. | |
| 7,091,127 B2 | 8/2006 | Hubbell et al. | |
| 7,132,475 B2 | 11/2006 | Hubbell et al. | |
| 7,291,673 B2 | 11/2007 | Hubbell et al. | |
| 7,427,410 B2 | 9/2008 | Hubbell et al. | |
| 7,744,912 B1 | 6/2010 | Hubbell et al. | |
| 9,271,929 B2 | 3/2016 | Dixon et al. | |
| 2002/0041898 A1 | 4/2002 | Unger et al. | |
| 2003/0044468 A1 | 3/2003 | Cellesi et al. | |
| 2003/0059906 A1 | 3/2003 | Hubbell et al. | |
| 2003/0086964 A1 | 5/2003 | Kwon et al. | |
| 2003/0133963 A1 | 7/2003 | Hubbell et al. | |
| 2003/0134420 A1 | 7/2003 | Lollo et al. | |
| 2003/0153001 A1 | 8/2003 | Soane et al. | |
| 2003/0166601 A1 | 9/2003 | Woodle et al. | |
| 2003/0215588 A1 | 11/2003 | Yeager et al. | |
| 2004/0204588 A1* | 10/2004 | DeLuca | |
| 2004/0234494 A1 | 11/2004 | Seo et al. | |
| 2004/0247624 A1 | 12/2004 | Unger et al. | |
| 2004/0258677 A1 | 12/2004 | Waldmann et al. | |
| 2005/0169899 A1 | 8/2005 | Diamond | |
| 2006/0057215 A1 | 3/2006 | Raiche et al. | |
| 2006/0057222 A1 | 3/2006 | Linhardt et al. | |
| 2006/0224095 A1 | 10/2006 | Claverie et al. | |
| 2006/0251710 A1 | 11/2006 | Kwon et al. | |
| 2007/0287672 A1 | 12/2007 | Creighton et al. | |
| 2008/0081074 A1 | 4/2008 | Gu et al. | |
| 2008/0097087 A1 | 4/2008 | Nagasaki et al. | |
| 2008/0293827 A1 | 11/2008 | Lee et al. | |
| 2010/0222407 A1 | 9/2010 | Segura et al. | |
| 2011/0223217 A1 | 9/2011 | Dixon et al. | |

FOREIGN PATENT DOCUMENTS

| | | |
|---|---|---|
| FR | 2809617 A1 | 12/2001 |
| GB | 1203577 A | 8/1970 |
| GB | 1348045 A | 3/1974 |
| WO | WO-95/13312 A1 | 5/1995 |
| WO | WO-97/15287 A1 | 5/1997 |
| WO | WO-97/22371 A1 | 6/1997 |
| WO | WO-98/05269 A1 | 2/1998 |
| WO | WO-98/16202 A2 | 4/1998 |
| WO | WO-98/32466 A1 | 7/1998 |
| WO | WO-99/14259 A1 | 3/1999 |
| WO | WO-99/22770 A1 | 5/1999 |
| WO | WO-99/34833 A1 | 7/1999 |
| WO | WO-00/09087 A1 | 2/2000 |
| WO | WO-00/44808 A1 | 8/2000 |
| WO | WO-00/71606 A1 | 11/2000 |
| WO | WO-01/02017 A2 | 1/2001 |
| WO | WO-01/32146 A2 | 5/2001 |
| WO | WO-01/92584 A1 | 12/2001 |
| WO | WO-01/93820 A1 | 12/2001 |
| WO | WO-02/055185 A2 | 7/2002 |
| WO | WO-03/024186 A2 | 3/2003 |
| WO | WO-03/024897 A2 | 3/2003 |
| WO | WO-03/087223 A1 | 10/2003 |
| WO | WO-2004/009664 A2 | 1/2004 |
| WO | WO-2005/068533 A1 | 7/2005 |
| WO | WO-2006/107311 A2 | 10/2006 |
| WO | WO-2006/109945 A1 | 10/2006 |
| WO | WO-2006/137855 A2 | 12/2006 |
| WO | WO-2006/137856 A2 | 12/2006 |
| WO | WO-2007/008300 A2 | 1/2007 |
| WO | WO-2007/043486 A1 | 4/2007 |
| WO | WO-2007/098254 A2 | 8/2007 |
| WO | WO-2010/068432 A1 | 6/2010 |

OTHER PUBLICATIONS

Bertrand et al., "Comparison of antisense oligonucleotides and siRNAs in cell culture and in vivo," Biochem Biophys Res Commun. 296(4):1000-4 (2002).

Blessing et al., "Different Strategies for Formation of PEGylated EGF-Conjugated PEI/DNA Complexes for Targeted Gene Delivery," Bioconjug Chem. 12(4):529-37 (2001).

Blume et al., "Specific targeting with poly(ethylene glycol)-modified liposomes: coupling of homing devices to the ends of the polymeric chains combines effective target binding with long circulation times," Biochim Biophys Acta. 1149(1):180-4 (1993).

Booth et al., "Effects of block architecture and composition on the association properties of poly(oxyalkylene) copolymers in aqueous solution," Macromol Rapid Commun. 21(9): 501-27 (2000).

Boyland et al., "Enzymes catalysing conjugations of glutathione with alpha-beta-unsaturated carbonyl compounds," Biochem J. 109(4):651-61 (1968).

Carlisle, "Use of adenovirus proteins to enhance the transfection activity of synthetic gene delivery systems," Curr Opin Mol Ther. 4(4):306-12 (2002).

Cerritelli et al., "Aggregation behavior of poly(ethylene glycol-bl-propylene sulfide) di- and triblock copolymers in aqueous solution," Langmuir. 25(19):11328-35 (2009).

Cerritelli et al., "PEG-SS-PPS: reduction-sensitive disulfide block copolymer vesicles for intracellular drug delivery," Biomacromolecules. 8(6):1966-72 (2007).

Cerritelli et al., "Thermodynamic and kinetic effects in the aggregation behavior of a poly(ethylene glycol-b-propylene sulfide-b-ethylene glycol) ABA triblock copolymer," Macromolecules 38:7845-51 (2005).

Chandaroy et al., "Utilizing temperature-sensitive association of pluronic F-127 with lipid bilayers to control liposome-cell adhesion," Biochim Biophys Acta. 1559(1):32-42 (2002).

Chasseaud, "Distribution of enzymes that catalyse reactions of glutathione with alpha beta-unsaturated compounds," Biochem J. 131(4):765-9 (1973).

Chen et al., "pH-responsive biodegradable micelles based on acid-labile polycarbonate hydrophobe: synthesis and triggered drug release," Biomacromolecules. 10(7):1727-35 (2009).

Cho et al., "Low molecular weight PEI conjugated pluronic copolymer: useful additive for enhancing gene transfection efficiency," Macromolecular Research. 14(3):348-53 (2006).

Czauderna et al., "Structural variations and stabilising modifications of synthetic siRNAs in mammalian cells," Nucleic Acids Res. 31(11):2705-16 (2003).

Dahlqvist et al., "The digestion and absorption of sucrose by the intact rat," J Physiol. 167:193-209 (1963).

Davies et al., "Self-assembly of surfactant vesicles that transform into viscoelastic wormlike micelles upon heating," J Am Chem Soc. 128(20):6669-75 (2006).

Deutsch et al., "Synthesis of congeners and prodrugs. 3. Water-soluble prodrugs of taxol with potent antitumor activity," J. Med. Chem. 32(4):788-92 (1989).

(56) References Cited

OTHER PUBLICATIONS

Discher et al., "Polymersomes: tough vesicles made from diblock copolymers," Science. 284(5417):1143-6 (1999).
Dumitriu et al., "Polymeric Drug Carriers," in *Polymeric Biomaterials*, Dumitriu, ed., pp. 435-449 and 466-724, Marcel Dekker, New York, 1994.
Duncan et al., "Soluble Synthetic Polymers as Potential Drug Carriers," Adv. in Polym. Sci. 57: 51-101, 1984.
East et al., "The Mannose Receptor Family," Biochim Biophys Acta. 1572(2-3):364-86 (2002).
Eisele et al., "Kinetics of photocrosslinking reactions of a DCPA/EA matrix in the presence of thiols and acrylates," J Polym Sci. 35(12): 2333-45 (1997).
Elbashir et al., "Duplexes of 21-nucleotide RNAs mediate RNA interference in cultured mammalian cells," Nature. 411(6836):494-8 (2001).
Erbacher et al., "Gene transfer by DNA/glycosylated polylysine complexes into human blood monocyte-derived macrophages," Hum Gene Ther. 7(6):721-9 (1996).
Fan et al., "Molecular recognition and catalysis: incorporation of an oxyanion hole into a synthetic receptor," New J. Chem. 21(1): 81-5 (1997).
Frankel et al., "Cellular Uptake of the Tat Protein from Human Immunodeficiency Virus," Cell. 55(6):1189-93 (1988).
Friedman et al., "Relative nucleophilic reactivities of amino groups and mercaptide ions in addition reactions with alpha-beta-unsaturated compounds," J Am Chem Soc. 87(16): 3672-82 (1965).
Gabizon et al., "Targeting Folate Receptor with Folate Linked to Extremities of Poly(ethylene glycol)-grafted Liposomes: In Vitro Studies," Bioconjugate Chem. 10(2):289-98 (1999).
Geng et al., "Hydrolytic degradation of poly(ethylene oxide)-block-polycaprolactone worm micelles," available in PMC Jan. 29, 2009, published in final edited form as: J Am Chem Soc. 127(37)12780-1 (2005) (7 pages).
Geng et al., "Shape effects of filaments versus spherical particles in flow and drug delivery," available in PMC Sep. 9, 2009, published in final edited form as: Nat Nanotechnol. 2(4):249-55 (2007) (15 pages).
Ghandehari et al., "In vitro degradation of pH-sensitive hydrogels containing aromatic azo bonds," Biomaterials. 18(12):861-72 (1997).
Gottschalk et al., "Folate Receptor Mediated DNA Delivery into Tumor Cells: Potosomal Disruption Results in Enhanced Gene Expression," Gene Ther. 1(3):185-91 (1994).
Green et al., "Autonomous Functional Domains of Chemically Synthesized Human Immunodeficiency Virus Tat Trans-activator Protein," Cell. 55(6):1179-88 (1988).
Greenwald et al., "Camptothecin-20-PEG Ester Transport Forms: the Effect of Spacer Groups on Antitumor Activity," Bioorg. Med. Chem. 6(5):551-62 (1998).
Greenwald et al., "Drug Delivery Systems: Water Soluble Taxol-2'-Poly(ethylene glycol) Ester Prodrugs-design and In Vivo Effectiveness," J. Med. Chem. 39(2):424-31 (1996).
Grünweller et al., "Comparison of different antisense strategies in mammalian cells using locked nucleic acids, 2'-O-methyl RNA, phosphorothioates and small interfering RNA," Nucleic Acids Res. 31(12):3185-93 (2003).
Han et al., "Oxidation-responsive micelles based on a selenium-containing polymeric superamphiphile," Langmuir. 26(18):14414-8 (2010).
Harbottle et al., "An RGD-oligolysine Peptide: a Prototype Construct for Integrin-mediated Gene Delivery," Hum Gene Ther. 9(7):1037-47 (1998).
Hartgerink et al., "Self-assembly and mineralization of peptide-amphiphile nanofibers," Science. 294(5547):1684-8 (2001).
Hern et al., "Incorporation of adhesion peptides into nonadhesive hydrogels useful for tissue resurfacing," J Biomed Mater Res. 39(2): 266-76 (1998).
Hirai et al., "Ph-induced Structure Change of Poly(vinyl alcohol) Hydrogel Crosslinked with Poly(acrylic acid)," Die Angewandte Makromolekulare Chemie. 240(1): 213-9 (1996).
Inoue et al., "Gene Therapy of Human Bladder Cancer with Adenovirus-mediated Antisense Basic Fibroblast Growth Factor," Clinical Cancer Research. 6(11):4422-31 (2000).
Inoue et al., "Nanometer-scale patterning of self-assembled monolayer films on native silicon oxide," Appl Phys Lett. 73(14):1976-8 (1998).
International Preliminary Report on Patentability for International Application No. PCT/US2014/048009, dated Jan. 26, 2016 (6 pages).
International Search Report and Written Opinion for International Application No. PCT/US14/48009, dated Oct. 27, 2014 (13 pages).
Ishihara et al., "Tris(pentafluorphenyl)boron as an efficient, air stable, and water tolerant lewis acid catalyst," Bull. Chem. Soc. Jpn. 68(6): 1721-30 (1995).
Jo et al., "RAFT homo- and copolymerization of N-acryloyl-morpholine, piperidine, and azocane and their self-assembled structures," Macromolecules. 41(4):1140-50 (2008).
Jousma et al., "Characterization of liposomes. The influence of extrusion of multilamellar vesicles through polycarbonate membranes on particle size, particle size distribution and number of bilayers," Int. J. Pharm. 35(3): 263-74 (1987).
Kabanov et al., "Pluronic® block copolymers as novel polymer therapeutics for drug and gene delivery," J Control Release. 82(2-3):189-212 (2002).
Kakizawa et al., "Block copolymer micelles for delivery of gene and related compounds," Adv Drug Deliv Rev. 54(2):203-22 (2002).
Katayose et al., "Water-soluble Polyion Complex Associates of DNA and Poly(ethylene glycol)-poly(L-lysine) Block Copolymer," Bioconjug Chem. 8(5):702-7 (1997).
Kawai et al., "New application of solid acid to carbon-carbon bond formation reactions: clay montmorillonite-catalyzed aldol reactions of silyl enol ethers with aldehydes and acetals," Bull. Chem. Soc. Jpn. 61(4): 1237-45 (1988).
Kenausis et al., "Poly(l-lysine)-g-poly(ethylene glycol) layers on metal oxide surfaces: Attachment mechanism and effects of polymer architecture on resistance to protein adsorption," J Phys Chem B. 104(14):3298-3309 (2000).
Kircheis et al., "Coupling of Cell-Binding Ligands to Polyethylenimine for Targeted Gene Delivery," Gene Ther. 4(5):409-18 (1997).
Kito et al., "Biocompatible Coatings for Luminal and Outer Surfaces of Small-caliber Artificial Grafts," J Biomed Mater Res. 30(3):321-30 (1996).
Kopecek et al., "Controlled release of drug model from N-(2-hydroxypropyl)-methacrylamide copolymers," Ann. N.Y. Acad. Sci. 446:93-104 (1985).
Kouwer et al., "Responsive biomimetic networks from polyisocyanopeptide hydrogels," Nature. 493(7434):651-5 (2013).
Lasic et al., Chapters 2, 4, and 9. *Stealth Liposomes*. CRC Press, 7-12, 25-33 and 93-102 (1995).
Lau et al., "Conjugation of doxorubicin to monoclonal anti-carcinoembryonic antigen antibody via novel thiol-directed cross-linking reagents," Bioorg. Med. Chem. 3(10):1299-304 (1995).
Lau et al., "Novel Doxorubicin-monoclonal Anti-carcinoembryonic Antigen Antibody Immunoconjugate Activity In Vitro," Bioorg. Med. Chem. 3(10)1305-12 (1995).
Libioulle et al., "Contact-inking stamps for microcontact printing of alkanethiols on gold," Langmuir. 15:300-4 (1999).
Liebau et al., "Microcontact Printing with Heavyweight Inks," Advanced Functional Materials. 11(2):147-50 (2001).
Loh et al., "The in vitro hydrolysis of poly(ester urethane)s consisting of poly[(R)-3-hydroxybutyrate] and poly(ethylene glycol)," Biomaterials. 27(9):1841-50 (2006).
Lv et al., "Toxicity of cationic lipids and cationic polymers in gene delivery," J Control Release. 114(1):100-9 (2006).
Mahmoud et al., "Inflammation responsive logic gate nanoparticles for the delivery of proteins," available in PMC Jul. 20, 2012, published in final edited form as: Bioconjug Chem. 22(7):1416-21 (2011) (19 pages).
Mathur et al., "Methods for Synthesis of Hydrogel Networks: A Review," J.M.S-Rev. Macromol. Chem. Phys. C 36(2): 405-30 (1996).
McCaffrey et al., "RNA interference in adult mice," Nature. 418(6893):38-9 (2002).

(56) References Cited

OTHER PUBLICATIONS

Moghaddam et al., "Molecular design of three-dimensional artificial extracellular-matrix: photosensitive polymers containing cell adhesive peptide," J. Polymer Sci. 31(6): 1589-97 (1993).
Morpurgo et al., "Preparation and characterization of poly(ethylene glycol) vinyl sulfone," Bioconjug. Chem. 7(3):363-8 (1996).
Mortensen, "Block copolymer in aqueous solution: micelle formation and hard-sphere crystallization," Prog Colloid Polym Sci. 93: 72-5 (1993).
Mühl et al., "Parallel nanolithography in carbon layers with conductive imprint stamps," Appl Phys Lett. 76(6):786-88 (2000).
Napoli et al., "Interfacial reactivity of block copolymers: understanding the amphiphile-to-hydrophile transition," Langmuir. 21(20):9149-53 (2005).
Napoli et al., "Lyotropic behavior in water of amphiphilic ABA triblock copolymers based on poly(propylene sulfide) and poly(ethylene glycol)," Langmuir. 18(22): 8324-9 (2002).
Napoli et al., "New synthetic methodologies for amphiphilic multiblock copolymers of Ethylene Glycol and Propylene Sulfide," Macromolecules. 34(26):8913-7 (2001).
Napoli et al., "Oxidation-responsive polymeric vesicles," Nat. Mater. 3(3):183-9 (2004).
NCBI Blast for Accession No. NP_001079500. Retrieved on Nov. 14, 2012 (2 pages).
Nuzzo et al., "Adsorption of bifunctional organic disulfides on gold surfaces," J Am Chem Soc. 105:4481-3 (1983).
Nuzzo et al., "Fundamental studies of the chemisorption of organosulfur compounds on Au(111). Implications for molecular self-assembly on gold surfaces," J Am Chem Soc. 109:733-40 (1987).
Pathak et al., "Rapid photopolymerization of immunoprotective gels in contact with cells and tissue," J Am Chem Soc. 114(21): 8311-2 (1992).
Pató et al., "Polymers containing enzymatically degradable bonds, 9a) chymotrypsin catalyzed hydrolysis of a p-nitroanilide drug model, bound via oligopeptides onto poly(vinylpyrrolidone-co-maleic anhydride)," Makromol Chem. 185(2): 231-7 (1984).
Pendri et al., "Antitumor Activity of Paclitaxel-2'-glycinate Conjugated to Poly(ethylene glycol): a Water-soluble Prodrug," Anticancer Drug Des. 13(5):387-95 (1998).
Petka et al., "Reversible Hydrogels from Self-assembling Artificial Proteins," Science. 281(5375):389-92 (1998).
Pitt et al., Controlled Drug Delivery. *Biodegradation of Polymers, Basic Concepts Volume 1*. CRC Press, 53-80 (1983).
Reich et al., "Small interfering RNA (siRNA) targeting VEGF effectively inhibits ocular neovascularization in a mouse model," Mol Vis. 9:210-6 (2003).
Romanowska et al., "Michael additions for syntheses of neoglycoproteins," Methods Enzymol. 242:90-101 (1994).
Rudra et al., "A self-assembling peptide acting as an immune adjuvant," Proc Natl Acad Sci U.S.A. 107(2):622-7 (2010).
Ryter et al., "Molecular basis of double-stranded RNA-protein interactions: structure of a dsRNA-binding domain complexed with dsRNA," EMBO J. 17(24): 7505-7513 (1998).
Saito et al., "Enhanced cytosolic delivery of plasmid DNA by a sulfhydryl-activatable listeriolysin O/protamine conjugate utilizing cellular reducing potential," Gene Ther. 10(1):72-83 (2003).
Sawhney et al., "Bioerodible hydrogels based on photopolymerized poly(ethylene glycol)-co-poly(alpha-hydroxy acid) diacrylate macromers," Macromolecules. 26(4): 581-7 (1993).
Segura et al., "Synthesis and in vitro characterization of an ABC triblock copolymer for siRNA delivery," Bioconjug Chem. 18(3):736-45 (2007).
Silva et al., "Selective differentiation of neural progenitor cells by high-epitope density nanofibers," Science. 303(5662):1352-5 (2004).
Simeoni et al., "Insight into the Mechanism of the Peptide-Based Gene Delivery System MPG: Implications for Delivery of siRNA into Mammalian Cells," Nucleic Acids Res. 31(11):2717-24 (2003).
Sowter et al., "Predominant role of hypoxia-inducible transcription factor (Hif)-1alpha versus Hif-2alpha in regulation of the transcriptional response to hypoxia," Cancer Res. 63(19): 6130-4 (2003).
Stouffer et al., "Polymer monolayers prepared by the spontaneous adsorption of sulfur-functionalized polystyrene on gold surfaces," Macromolecules. 21(5):1204-8 (1988).
Strickley, "Solubilizing excipients in oral and injectable formulations" Pharm Res. 21(2):201-30 (2004).
Tam-Chang et al., "Self-assembled monolayers on gold generated from alkanethiols with the structure $RNHCOCH_2SH$," Langmuir. 11:4371-82 (1995).
Tanaka et al., "Michael-type addition of illudin S, a toxic substance from Lampteromyces japonicus, with cysteine and cysteine-containing peptides In vitro, " Chem Pharm Bull (Tokyo). 44(2):273-9 (1996).
Tarasov et al., "Structural plasticity of a transmembrane peptide allows self-assembly into biologically active nanoparticles," Proc Natl Acad Sci U.S.A. 108(24):9798-803 (2011).
Thumshirn et al., "Multimeric cyclic RGD peptides as potential tools for tumor targeting: solid-phase peptide synthesis and chemoselective oxime ligation," Chemistry 9(12):2717-25 (2003).
Torchilin et al., "Poly(ethylene glycol) on the Liposome Surface: on the Mechanism of Polymer-coated Liposome Longevity," Biochim Biophys Acta. 1195(1):11-20 (1994).
Vasdekis et al., "Precision intracellular delivery based on optofluidic polymersome rupture," ACS Nano. 6(9):7850-7 (2012).
Velluto et al., "PEG-b-PPS diblock copolymer aggregates for hydrophobic drug solubilization and release: cyclosporin A as an example," Mol Pharm. 5(4):632-42 (2008).
Walker et al., "Toward synthetic viruses: endosomal pH-triggered deshielding of targeted polyplexes greatly enhances gene transfer in vitro and in vivo," Mol Ther. 11(3):418-25 (2005).
Watanabe et al., "First example of photoinduced copolymerizability enhancement. Copolymerization of epoxide and episulfide initiated with zinc N-substituted porphyrin under visible light irradiation," Macromolecules. 24(13): 3970-2 (1991).
Webber et al., "Controlled release of dexamethasone from peptide nanofiber gels to modulate inflammatory response," available in PMC Oct. 1, 2013, published in final edited form as: Biomaterials. 33(28):6823-32 (2012) (21 pages).
West et al., "Comparison of covalently and physically cross-linked polyethylene glycol-based hydrogels for the prevention of postoperative adhesions in a rat model," Biomaterials. 16(15): 1153-6 (1995).
Wilson et al., "Orally delivered thioketal-nanoparticles loaded with TNFalpha-siRNA target inflammation and inhibit gene expression in the intestines," available in PMC Jul. 23, 2011, published in final edited form as: Nat Mater. 9(11):923-8 (2010) (13 pages).
Won et al., "Giant wormlike rubber micelles," Science. 283(5404):960-3 (1999).
Wright et al., Chapter 3.3: Prodrugs of Paclitaxel; Chapter 5: Paclitaxel (Taxol®) Chemistry and Structure-Activity Relationships; Chapter 6: The Chemistry of the Taxol® Side Chain: Synthesis, Modifications and Conformational Studies. *The Chemistry and Pharmacology of Taxol® and Its Derivatives*. Farina, ed., pp. 110-130 and 165-300, Elsevier, New York, 1995.
Yu et al., "Bilayer morphologies of self-assembled crew-cut aggregates of amphiphilic PS-b-PEO diblock copolymers in solution," Macromolecules. 31(11): 3509-18 (1998).
Zalipsky et al., "Attachment of drugs to polyethylene glycols," Eur Polym J. 19(12): 1177-83 (1983).
Zalipsky et al., "Peptide Attachment to Extremities of Liposomal Surface Grafted PEG Chains: Preparation of the Long-circulating Form of Laminin Pentapeptide, YIGSR," Bioconjug Chem. 6(6):705-8 (1995).
Zalipsky et al., "Long-circulating, polyethylene glycol-grafted immunoliposomes," J Control Release. 39(2):153-61 (1996).
Zhao et al., "Novel degradable PEG esters for drug delivery: synthesis and characterization," Polymer Reprints 38:526-7 (1997).
Zhou et al., "Self-Assembly in a Mixture of Two Poly(Ethylene Oxide)-b-Poly(Propylene Oxide)-b-Poly(Ethylene Oxide) Copolymers in Water," J Colloid Interface Sci. 183(2):339-50 (1996).

* cited by examiner

HIGH ASPECT RATIO NANOFIBRIL MATERIALS

CROSS-REFERENCE TO RELATED APPLICATIONS

This application claims the benefit of U.S. Provisional Application No. 61/858,314, filed Jul. 25, 2013, which is hereby incorporated by reference in its entirety.

BACKGROUND OF THE INVENTION

Supramolecular self-assembly of amphipathic block copolymers has been utilized to generate nano- and microscale materials with controllable architectures. By controlling block and polymer characteristics including chemical composition, relative hydrophobicity and hydrophilicity, and absolute and relative block size, spherical micellar, linear fibrillar, and spherical vesicular architectures can be accessed.

Supramolecular assemblies can be created from homogeneous or heterogeneous mixtures of molecular precursors containing synthetic oligomer and polymer, polypeptide, and lipid components. A wide range of biomedical applications have been found for these soft materials; of particular interest are stimulus-responsive materials, in which changes in assembly architecture and/or biological activity are dictated by external stimuli which may include pH, redox status, or enzymatic function.

Chemical composition represents a defining characteristic of constituent molecules designed to undergo supramolecular self-assembly. In assemblies destined for biological applications, and in constituent molecules composed of synthetic polymer, the biocompatible polymer poly(ethylene glycol) (PEG) is a common component. Presentation of PEG surface chemistry to the biological environment limits recognition by phagocytes and increases material lifetime upon injection or implantation. For the preparation of block copolymer amphiphiles that yield micellar, fibrillar, and vesicular architectures upon self-assembly (Cerritelli et al., 2009), PEG-based macroinitiators have been utilized for ring-opening polymerizations of the monomer propylene sulfide.

In comparison to the spherical architecture of micellar and vesicular self-assembly architectures, linear fibrillar (or "worm-like") structures enable a wider variety of downstream material applications and biological performance characteristics. Self-assembled materials relevant for biological applications are typically defined by presentation of a hydrophilic surface, with self-assembly at least partially driven by hydrophobic interactions and avoidance of the aqueous environment. Amphiphilic linear fibril precursors are defined by a variety of molecular components including synthetic polymers (Geng and Discher, 2005), polypeptides (Rudra et al., 2010), and peptide-lipid constructs (Hartgerink et al., 2001). Fibrillar platforms have been utilized in vivo with methodologies analogous to those optimized for micellar/vesicular platforms; for example, in the context of injectable small molecule carriers. When injected intravenously, polymer-based, hydrolysis-sensitive linear fibrils are capable of circulating in the blood as spherical materials do, but with very different circulation behaviors (Geng et al., 2007). Assembly or cross-linking of fibrillar assemblies also permits formation of bulk three-dimensional structures, for molecular depot or synthetic matrix applications. For example, Webber et al. employed assembly of pre-formed peptide-lipid amphiphiles to create dexamethasone-releasing gels (Webber et al., 2012), while Silva et al. utilized cross-linked fibril assemblies prepared from related materials for neural progenitor cell differentiation (Silva et al., 2004). The helical conformation of polyisocyanopeptides grafted with oligo(ethylene glycol) yielded thermally-responsive filamentous structures capable of extracellular matrix-mimetic hydrogel formation (Kouwer et al., 2013).

In addition to establishing defined control over the formation of self-assembled supramolecular architectures, it is valuable to define disassembly or degradation mechanisms by choice of material chemistries. A spectrum of defined control exists, ranging from relatively non-specific thermal or light sensitivity and hydrolytic susceptibility, to biologically-relevant pH or redox dependence, to highly-specific conformal or enzymatic reactivity. Previously, light sensitivity (Vasdekis et al., 2012), oxidative sensitivity (Napoli et al., 2004), and redox sensitivity (Cerritelli et al., 2007) have been explored in vesicular assemblies derived from PEG-poly(propylene sulfide). Material sensitivity to redox status in particular is relevant both in the context of inflammation in the extracellular environment and post-phagocytic lysosomal processing in the intracellular environment. Han and coworkers developed hydrogen peroxide-responsive selenium-containing polymer micelle constructs assembled from electrostatic interactions (Han et al., 2010). In another approach, Mahmoud et al. utilized emulsion solvent evaporation to prepare hydrogen peroxide-sensitive micelles for protein delivery (Mahmoud et al., 2011). Both thioketal-containing nanoparticles (Wilson et al., 2010) and thioether-containing micellar constructs (Segura and Hubbell, 2007) have been generated for intracellular siRNA delivery from oxidation-sensitive particles. Exquisite sensitivity to the biological environment has been demonstrated in nanoparticles assembled from CXCR4-derived transmembrane peptide; peptide conformational change is associated with nanoparticle disassembly and spontaneous fusion with cell membrane (Tarasov et al., 2011).

SUMMARY OF THE INVENTION

We describe linear and three-dimensional supramolecular fibril materials self-assembled from block copolymers comprising oligo(ethylene sulfide) (OES). We address amphiphilic block copolymer fibril constituents that upon self-assembly are capable of forming both water-suspendable linear structures as well as cross-linked bulk three-dimensional structures. The fibrillar materials are sensitive to oxidation, which leads to decreased OES block hydrophobicity and crystallinity, and increased water solubility of the polymer constituents. Molecular loading options, coupled with oxidative sensitivity, allow implantable or injectable fibril suspensions or cross-linked three-dimensional matrices to demonstrate significant biomedical potential, especially in the context of extracellular and intracellular molecular delivery and applications related to infection and disease.

In general, the present invention relates to a block copolymer including a hydrophilic block and an oligo(ethylene sulfide) (OES) block, supramolecular assemblies thereof, and methods of their use.

In a first aspect, the invention provides a block copolymer including a hydrophilic block and an oligo(ethylene sulfide) (OES) block. In some embodiments, the hydrophilic block is selected from the group consisting of poly(ethylene oxide)-co-poly(propylene oxide) random, di- or multiblock copolymers, poly(ethylene oxide) (PEG), poly(vinyl alcohol), poly(ethylene-co-vinyl alcohol), poly(N-vinyl pyrrolidone), poly(acrylic acid), poly(methyloxazoline) (PMOXA), poly(ethyloxazoline), poly(alkylacrylates), poly(acrylamide), poly(N-alkylacrylamides), hydrophilic polypeptide, polysaccharide, poly(N,N-dialkylacrylamides), hyaluronic acid, alginate, cyclodextrin, or poly (N-acryloylmorpholine). In particular embodiments, the hydrophilic block is PEG. In certain embodiments, the PEG is of molecular weight 500 to 50,000. In other embodiments, the degree of polymerization of the OES block is 2 to 10. In yet other embodiments, the block copolymer is linear. In still other embodiments, the block copolymer is branched (e.g., a multi-arm copolymer). In particular embodiments, the block copolymer further contains a moiety selected from a fluorophore; a protecting group; peptide; chemokine; pharmaceutically-relevant small molecule drug; adjuvant molecule including Toll-like receptor ligands, other pathogen-associated molecular patterns (PAMPs), and damage-associated molecular patterns (DAMPs); natural or recombinant protein or protein conjugate; sugar, saccharide, or carbohydrate; synthetic polymer; and conjugates thereof covalently attached to the hydrophilic block or the OES block.

In a second aspect, the invention provides a supramolecular assembly containing a plurality of block copolymers of the first aspect (e.g., dispersed in a liquid or gel). In some embodiments, the assembly is a fibril, rod, or micelle. In other embodiments, the assembly is a matrix. In certain embodiments, the plurality of block copolymers comprises linear and branched copolymers self-assembled or covalently linked to form the matrix. In particular embodiments, the supramolecular assembly further contains a second polymer matrix, e.g., poly(acrylamide). In other embodiments, the second polymer matrix forms a polymer interpenetrating network with the plurality of block copolymers. In yet other embodiments, the block copolymers form fibrils that are dispersed in the second polymer matrix. In still other embodiments, the supramolecular assembly further includes a hydrophobic or amphoteric molecule dissolved or dispersed in the assembly (e.g., the hydrophobic or amphoteric molecule is selected from the group consisting of a fluorophore; peptide; chemokine; pharmaceutically-relevant small molecule drug; adjuvant molecule including Toll-like receptor ligands, other PAMPs, and DAMPs; and conjugates thereof).

In a third aspect, the invention provides a method of delivering a target molecule to a subject, the method including providing a supramolecular assembly of the second aspect, in which the supramolecular assembly contains the target molecule; and contacting the subject with the supramolecular assembly, thereby delivering the target molecule to the subject. In some embodiments, the target molecule is covalently attached to the supramolecular assembly. In certain embodiments, the target molecule is a hydrophobic molecule dissolved or dispersed in the supramolecular assembly. In further embodiments, the supramolecular assembly is a depot deposited internally in the subject. In particular embodiments, the supramolecular assembly is dispersed in a liquid carrier when contacted with the subject.

In some embodiments, the supramolecular assembly is for use as a medicament.

In a fourth aspect, the invention provides use of a supramolecular assembly of the second aspect in the manufacture of a medicament.

In a fifth aspect, the invention provides a pharmaceutical composition containing the supramolecular assembly of the second aspect and a pharmaceutically acceptable carrier.

DETAILED DESCRIPTION OF THE INVENTION

Figure 1:
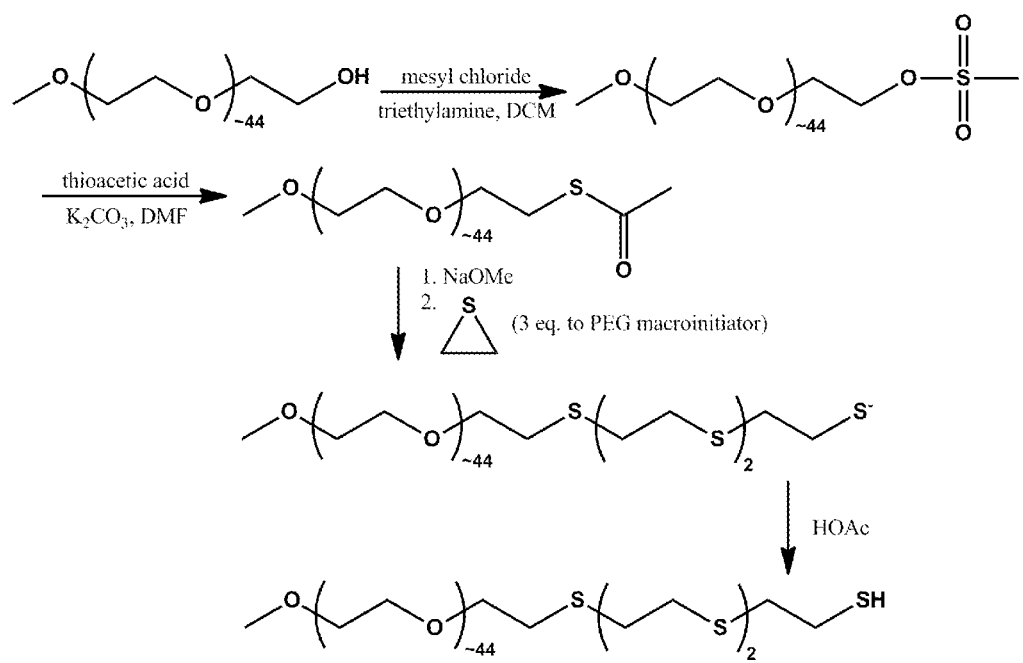
FIG. 1. Oligomerization of ethylene sulfide from PEG macroinitiator, for preparation of $PEG_{44}$-$OES_3$.

We describe block copolymers including a hydrophilic block and an oligothioether block, where the oligothioether block includes oligo(ethylene sulfide), and assembly of these block copolymers into fibrillar architectures. In particular, we expand the self-assembly capabilities of PEG-thioether block copolymer amphiphiles by replacing propylene sulfide with a related but previously unexplored monomer, ethylene sulfide. Oligo- and poly(ethylene sulfide) is obtained through cationic or anionic ring-opening polymerization of the cyclic ethylene sulfide monomer. In polymer form, ethylene sulfide is a hydrophobic and highly crystalline molecule. The instant invention demonstrates that under self-assembly conditions, these characteristics drive formation of supramolecular structures, given appropriate relative molecular weights of the PEG and oligo(ethylene sulfide) blocks. The instant invention demonstrates that even very low degrees of polymerization of ethylene sulfide provide very stable self-assembled structures.

A convenient hydrophilic block is poly(ethylene glycol) (PEG), and other synthetic or natural hydrophilic polymers may be used. The PEG-oligothioether copolymer is composed of the hydrophilic PEG block, covalently attached to a hydrophobic block composed of OES. The free PEG terminus not connected to the hydrophobic block may be one of a number of chemical groups, including but not limited to hydroxyl, methoxy, thiol, amine, maleimide, halogen, protecting group, drug, or biomolecule. Both blocks may vary in molecular weight and therefore size, the adjustment of which alters block copolymer amphiphilic behavior. A preferred embodiment is a linear PEG-OES block copolymer whose relative block sizes yield formation of supramolecular linear fibrillar (high-aspect ratio) architecture following self-assembly. A preferred embodiment of the self-assembly of PEG-OES block copolymers into supramolecular fibrillar architectures is driven by enthalpically favorable crystallization of the hydrophobic ethylene sulfide domain, for example through emulsion solvent evaporation from immiscible organic and aqueous cosolvents, or for example from thin film evaporation. A special feature of the invention is that self-assembly is driven by both hydrophobicity and crystallization of the OES block, and the energetic contribution of crystallization drives formation of supramolecular structures at much smaller OES block lengths than would be necessary with amorphous analogs such as oligo(propylene sulfide) or poly(propylene sulfide) (these denominations are used interchangeably herein). Moreover, the formed supramolecular structures are more stable to dissociation than those formed with the amorphous analogs. Linear high-aspect-ratio organic materials are utilized as components to, for example, increase mechanical strength of heterogeneous materials. A preferred embodiment is formation of covalent polymer networks in the presence of self-assembled linear fibrils generated from linear PEG-OES block copolymer.

Preparation of three-dimensional fibrillar matrices is achieved following self-assembly of branched and/or multi-arm PEG-OES block copolymers. A preferred embodiment of the multivalent PEG-OES block copolymer is a branched and/or multi-arm PEG core, variant both of absolute size and of molecular weight between branches, in which three or greater branches or arms terminate in an OES block of appropriate molecular weight to allow self-assembly formation of a fibrillar matrix, using techniques described above for linear supramolecular assemblies. In a preferred embodiment, fibrillar matrices are achieved by assembly of branched or multi-arm constituent block copolymer in the presence or absence of co-assembly with linear constituent block copolymer that forms linear fibril assemblies. Matrices are also achieved by covalently cross-linking pre-formed linear fibril architectures with a network-forming component that presents two or more sites for conjugation to reactive sites on the formed fibrils. A preferred embodiment is linear fibril assemblies connected by a bi- or multi-valent natural or synthetic polymer, a polysaccharide, a natural or recombinant protein or protein conjugate, and/or another pre-formed fibril assembly. Heterogeneous polymer-derived networks are generated by initial formation of one cross-linked matrix structure, followed by formation of an interpenetrating network via matrix formation from secondary polymer component. Thus a preferred embodiment of three-dimensional fibrillar matrix formation is formation of interpenetrating polymer networks (IPNs), in which the three-dimensional fibrillar matrix is formed in either the initial or secondary network formation step.

Building from the linear and branched/multi-arm PEG-OES block copolymers described above, the constituent polymer may undergo covalent modification prior to supramolecular assembly into linear or branched fibril structures. Covalent modification may occur at one or more termini; in the case of multiple modifications, the modifying moieties may be the same or different. In a preferred embodiment, a modifying moiety may include but is not limited to a fluorophore; a protecting group; peptide; chemokine; pharmaceutically-relevant small molecule drug; adjuvant molecule including Toll-like receptor ligands, other pathogen-associated molecular patterns (PAMPs), and damage-associated molecular patterns (DAMPs); natural or recombinant protein or protein conjugate; sugar, saccharide, or carbohydrate;

synthetic polymer; and conjugates thereof. In a preferred embodiment, supramolecular linear fibril assemblies and three-dimensional fibril networks may be generated via self-assembly of one or more unmodified or modified linear, branched, or multi-arm constituent block copolymers.

Molecular modification of supramolecular fibril structures, in both high-aspect-ratio linear assemblies and three-dimensional fibril networks, is also achieved through a process of initial fibril and/or network self-assembly followed by covalent modification. In a preferred embodiment, a modifying moiety may include but is not limited to a fluorophore; peptide; chemokine; pharmaceutically-relevant small molecule drug; adjuvant molecule including Toll-like receptor ligands, other PAMPs, and DAMPs; natural or recombinant protein or protein conjugate; sugar, saccharide, or carbohydrate; synthetic polymer; and conjugates thereof. Multiple and sequential fibril modifications are achieved by removing chemical protecting groups with subsequent modification.

Incorporation of hydrophobic small molecules into the hydrophobic OES supramolecular core yields non-covalent molecular modification of linear fibril assemblies and three-dimensional fibril networks. In a preferred embodiment, a linear fibril or three-dimensional fibril network is initially formed, into which one or more hydrophobic small molecules are allowed to diffuse. Alternatively, one or more hydrophobic small molecules is dissolved in the organic solvent phase used to prepare fibril assemblies through emulsion solvent evaporation or thin film evaporation. In a preferred embodiment, one or more small hydrophobic molecules are represented by a fluorophore; peptide; chemokine; pharmaceutically-relevant small molecule drug; adjuvant molecule including Toll-like receptor ligands, other PAMPs, and DAMPs; and conjugates thereof, and their incorporation into the hydrophobic core domain of the linear fibril assembly or three-dimensional fibril network does not interfere with or prevent assembly.

As described above, there are myriad permutations for assembly and for covalent and non-covalent modification of fibril-constituent block copolymer species. The invention includes assemblies generated from any individual or combination of step-wise modification. This includes heterogeneous linear or matrix assemblies containing unmodified and/or differently modified constituent polymers; assemblies may also be subsequently modified or loaded.

Fibril degradation or disassembly mechanism represents an important aspect of fibril performance, for material processing or downstream biological applications. In a preferred embodiment, oxidative conditions promote fibril disassembly by progressive chemical conversion of hydrophobic and crystal-forming ethylene sulfide residues (or mers) to increasingly hydrophilic and decreasingly crystalline sulfoxide and sulfone groups. Within the constituent block copolymers, subsequent and progressive loss of amphiphilic behavior without chain scission promotes fibril disassembly and formation of populations heterogeneous with micellar constructs, then to loss of supramolecular architectures (Napoli et al., 2005). In a preferred embodiment, oxidative sensitivity of the fibrillar materials will be utilized to promote disassembly in the extracellular environment in the presence of reactive oxygen species. In an additional preferred embodiment, redox sensitivity of the fibrillar materials will be utilized to promote disassembly in the intracellular environment, in the context of endolysosomal processing subsequent to cellular uptake via phagocytic mechanisms. In a preferred embodiment, chemical treatment (oxidizing conditions) or physical processing (lyophilizing) promotes fibril shortening to rod-like structures and micelles.

Although the above description refers to PEG as the hydrophilic block, other hydrophilic polymers may be used in place of PEG including poly(ethylene oxide)-co-poly (propylene oxide) random, di- or multiblock copolymers, poly(ethylene oxide), poly(vinyl alcohol), poly(ethylene-co-vinyl alcohol), poly(N-vinyl pyrrolidone), poly(acrylic acid), poly(methyloxazoline) (PMOXA), poly(ethyloxazoline), poly(alkylacrylates), poly(acrylamide), poly(N-alkylacrylamides), hydrophilic polypeptides, polysaccharides, poly(N,N-dialkylacrylamides), hyaluronic acid, alginate, cyclodextrin, or poly (N-acryloylmorpholine). The hydrophilic block may be present at a molecular weight of between 500 and 50,000. The OES block may have between 2 and 50 monomer units (e.g., between 3 and 40 monomer units, 3 and 30 monomer units, or 3 and 20 monomer units).

The block copolymers of the invention can be used to form supramolecular assemblies (e.g., fibrils, rods, or matrices), e.g., in liquids or gels. The supramolecular assemblies of the invention, when dispersed in a second polymer matrix, can form, e.g., fibril-embedded or interpenetrating matrices. Suitable second polymer matrices include gels. Gels that may be used to prepare the supramolecular assemblies of the invention include those from poly(acrylic acid), poly(saccharides) (e.g., alginic acid, carboxymethylcellulose, ethylcellulose, hydroxyethylcellulose, hydroxypropyl cellulose, methylcellulose, tragacanth gum, xanthan gum or sodium alginate), polypeptides (e.g., gelatin), poloxamers, poly(vinyl alcohol), and poly(acrylamide), and mixtures thereof (e.g., acacia gum). In certain embodiments, the second polymer matrix includes poly(acrylamide).

The block copolymers of the invention can be used for the encapsulation of pharmaceutical agents such as peptides, nucleic acids, antibiotics (e.g., ampicillin or tetracycline), chemotherapeutics (e.g., doxorubicin), or other small molecule pharmaceutical agents. Pharmaceutical compositions may also employ excipients that increase the encapsulation efficiency of one or more block copolymers for pharmaceutical agents that are hydrophilic, hydrophobic, or amphiphilic. The excipients may increase the compatibility of the pharmaceutical agent with one or more blocks in the block copolymer, e.g., by reducing repulsive forces or increasing attractive forces between the pharmaceutical agent and one or more blocks of the block copolymer.

Suitable exemplary excipients are 1,8-diazabicyclo[5.4.0] undec-7-ene (DBU) and polyethylene glycol (e.g., PEG 600). PEG having a molecular weight between 400 and 800 Da is effective as an excipient. Other excipients that may be used are PPS-PEG copolymers and hydrobromide or hydrochloride salts of common organic bases such as triethanolamine, triethylamine, or pyridine. The addition of an excipient to a mixture containing a block copolymer and a pharmaceutical agent may increase the efficiency of encapsulation of the pharmaceutical agent by greater than 1.5-fold, 3-fold, 5-fold, 10-fold, or 50-fold.

In various embodiments, the pharmaceutical composition includes about 1 ng to about 20 mg of pharmaceutical agent, e.g., a nucleic acid or a hydrophobic compound (e.g., paclitaxel or dexamethasone). In some embodiments, the composition contains about 10 ng to about 10 mg, about 0.1 mg to about 500 mg, about 1 mg to about 350 mg, about 25 mg to about 250 mg, or about 100 mg of pharmaceutical agents. Those of skill in the art of clinical pharmacology can readily arrive at dosing amounts using routine experimentation.

Suitable carriers include, but are not limited to, saline, buffered saline, dextrose, water, glycerol, ethanol, and combinations thereof. The composition can be adapted for the mode of administration and can be in the form of, for example, a pill, tablet, capsule, spray, powder, or liquid. In some embodiments, the pharmaceutical composition contains one or more pharmaceutically acceptable additives suitable for the selected route and mode of administration. These compositions may be administered by, without limitation, any parenteral route including intravenous, intraarterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g., mammalian) subjects in the form of liquids, including sterile, non-pyrogenic liquids for injection, emulsions, powders, aerosols, tablets, capsules, enteric coated tablets, or suppositories. Conventional procedures and ingredients for the selection and preparation of suitable formulations are described, for example, in Remington's Pharmaceutical Sciences (2003-20th edition) and in The United States Pharmacopeia: The National Formulary (USP 24 NF19), published in 1999.

Pharmaceutical agents may be hydrophilic, hydrophobic, or amphoteric. Typically, hydrophilic agents will be covalently attached to the copolymer, and hydrophobic agents will be encapsulated in the interior of an assembly. Agents that may be employed with copolymers of the invention include but are not limited to natural and synthetic compounds, e.g., a nucleic acid, having the following therapeutic activities: anti-arthritic, anti-arrhythmic, anti-bacterial, anti-cholinergic, anticancer, anticoagulant, antidiuretic, antidote, antiepileptic, antifungal, anti-inflammatory, antimetabolic, antimigraine, antineoplastic, antiparasitic, antipyretic, anti-seizure, antisera, antispasmodic, analgesic, anesthetic, beta-blocking, biological response modifying, bone metabolism regulating, cardiovascular, diuretic, enzymatic, fertility enhancing, growth-promoting, hemostatic, hormonal, hormonal suppressing, hypercalcemic alleviating, hypocalcemic alleviating, hypoglycemic alleviating, hyperglycemic alleviating, immunosuppressive, immunoenhancing, muscle relaxing, neurotransmitting, parasympathomimetic, sympathominetric plasma extending, plasma expanding, psychotropic, thrombolytic, chemotherapeutic, and vasodilating.

EXAMPLES

Example 1: Preparation of Linear PEG-OES and OES-PEG-OES Block Copolymers by Ring-Opening Oligomerization of Ethylene Sulfide from PEG Macroinitiator Using monomethoxy-terminated PEG (MW 2000) as the starting material, a monomethoxy-PEG-thioacetate macroinitiator species was prepared according to previously described methods (Napoli et al., 2001; Velluto et al., 2008). Monomethoxy-PEG-thioacetate was transferred to Schlenk tube under argon and dissolved in tetrahydrofuran. The solution was stirred at room temperature under argon for thirty minutes following addition of 1.1 equivalents sodium methoxide (0.5 M solution in methanol). After sodium methoxide activation, various equivalents (2, 3, or 4) of cyclic ethylene sulfide monomer were added. The reaction was terminated by adding excess glacial acetic acid (FIG. 1). The constituent block copolymer was obtained after washing, filtration, precipitation in diethyl ether, and vacuum drying. This technique is easily expanded to a wide range of alternatively-terminated PEG starting materials; for example, with fluorescent labels or protecting groups replacing the methoxy group described above. After drying, PEG-OES block copolymer was obtained in 80-90% yield and analyzed by 1H-NMR (400 MHz, CDCl$_3$) $\delta$3.83-3.44 (s, OCH$_2$CH$_2$), 3.37 (s, OCH$_3$), 2.87 (td, CH$_2$SH) 2.81-2.72 (m, SCH$_2$CH$_2$). With target ethylene sulfide degree of polymerization (DP)=2 from MW 2000 macroinitiator, observed DP in block copolymer samples was a mixture of 1 and 2. Target DP=3 was consistently obtained in ethylene sulfide oligomerization from MW 2000 macroinitiator. Initiation of oligomerization from MW 2000 macroinitiator with target DP=4 led to irreversible precipitation of organic solvent-insoluble polymer product. Initiation of oligomerization from MW 5000 macroinitiator of ethylene sulfide DP=3 and 4 is feasible. These examples demonstrate that for downstream self-assembly, design and synthesis of block copolymers comprised of oligo(ethylene sulfide) is a balance between controlling defined block size, and avoiding irreversible polymer precipitation. OES-PEG-OES having the theoretical formula of H(SCH$_2$CH$_2$)$_3$S(CH$_2$CH$_2$O)$_{-134}$CH$_2$CH$_2$S(CH$_2$CH$_2$S)$_3$H was prepared following a similar procedure in which the starting material was dihydroxyl-terminated PEG.

Example 2: Preparation of Linear OES Copolymers with other Hydrophilic Polymers

Figure 2:
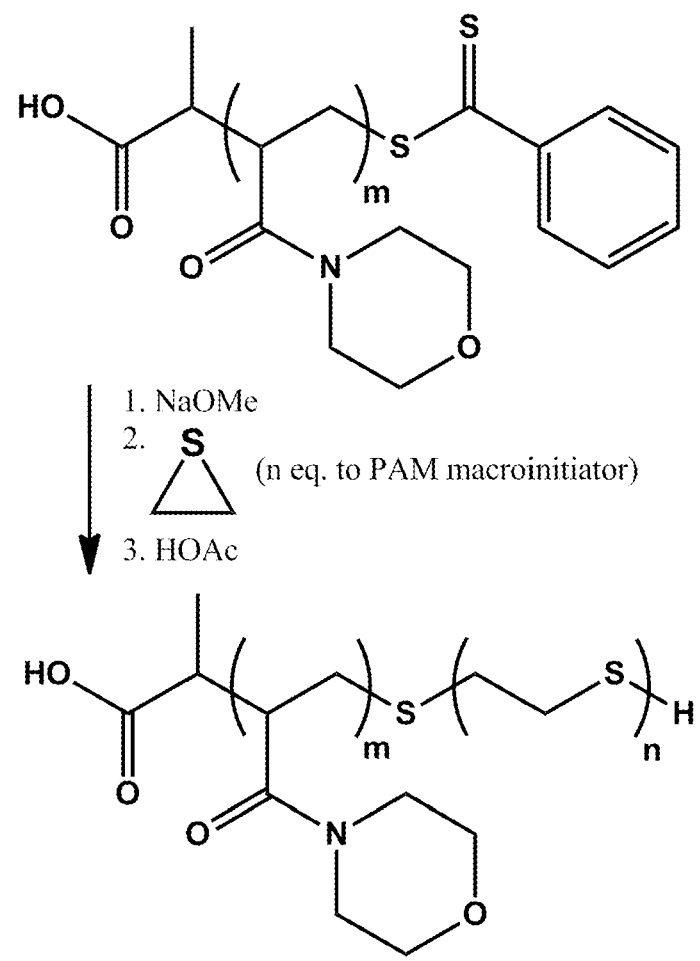
FIG. 2. Preparation of block copolymer amphiphile PAM-OES.

Synthetic polymers besides PEG may be utilized as the hydrophilic block of the fibril constituent amphiphilic block copolymer. For example, it has previously been shown that diblock copolymers in which poly(acryloylmorpholine) (PAM) represents the hydrophilic block are capable of forming nanoscale self-assembled micellar constructs (Jo et al., 2008). In this approach, PAM homopolymers and diblock copolymers are synthesized by reversible addition-fragmentation chain-transfer polymerization (RAFT). In order to obtain PAM-OES constructs, the technique is modified, utilizing a two-step process involving (1) PAM homopolymerization by RAFT followed by (2) ring-opening oligomerization of ethylene sulfide using PAM as the macroinitiator (FIG. 2). PAM homopolymerization was described (Jo et al., 2008); briefly, N-acryloylmorpholine monomer and 2-[(2-phenyl-1-thioxo)thio]propanoic acid chain transfer agent are dissolved in 1,4-dioxane. Following evacuation, polymerization proceeded at 90° C. for 24 hr, and polymers are obtained by precipitation in diethyl ether and vacuum drying. PAM homopolymer presents a labile terminal phenyldithioester; after dissolving in tetrahydrofuran under argon atmosphere, activation with 1.1 equivalents sodium methoxide (0.5 M solution in methanol) to the PAM macroinitiator yields a terminal thiolate. Addition of ethylene sulfide monomer yields ring-opening polymerization that is quenched with excess glacial acetic acid. Both RAFT and ring-opening polymerization permit narrow control over absolute and relative block molecular weight and therefore size. Indeed, PAM homopolymers of approximately 7000 MW have been obtained with low dispersity (Jo et al., 2008). These values are directly relevant for adaptation to amphiphilic PAM-OES block copolymers capable of undergoing self-assembly.

Example 3: Preparation of Multi-Arm PEG-OES Block Copolymer by Ring-Opening Oligomerization of Ethylene Sulfide from Multi-Arm PEG Macroinitiator Using hydroxy-terminated branched or multi-arm PEG as the starting material, thioacetate-terminated branched or multi-arm PEG macroinitiator species were prepared, as in Example 1. In this example, four-arm MW 15000 starting material was used, although branched or multi-arm PEG MW 10000 and 20000 are feasible. The thioacetate-terminated four-arm PEG MW 15000 macroinitiator was transferred to Schlenk tube under argon and dissolved in tetrahydrofuran. The solution was stirred at room temperature under argon for thirty minutes following addition of 1.1 equivalents sodium methoxide (0.5 M solution in methanol) per arm. After sodium methoxide activation, 3 equivalents of cyclic ethylene sulfide monomer per arm were added. The reaction was terminated by adding excess glacial acetic acid. The multi-arm block copolymer was obtained after washing, filtration, precipitation in diethyl ether, and vacuum drying. After drying, block copolymer was obtained in 70-80% yield and analyzed by 1H-NMR (400 MHz, CDCl$_3$) $\delta$3.82-3.42 (s, OCH$_2$CH$_2$), 2.87 (td, CH$_2$SH) 2.79-2.72 (m, SCH$_2$CH$_2$). Extending from this example, oligomerization of ethylene sulfide with DP=4 per arm is also feasible. Similarly, a four-arm OES-terminated precursor having a theoretical formula of C[(CH$_2$CH$_2$O)$_{-112}$CH$_2$CH$_2$S(CH$_2$CH$_2$S)$_3$H]$_4$ was prepared.

Example 4: Production of Linear Macromolecular Fibril Assembly

Figure 3:
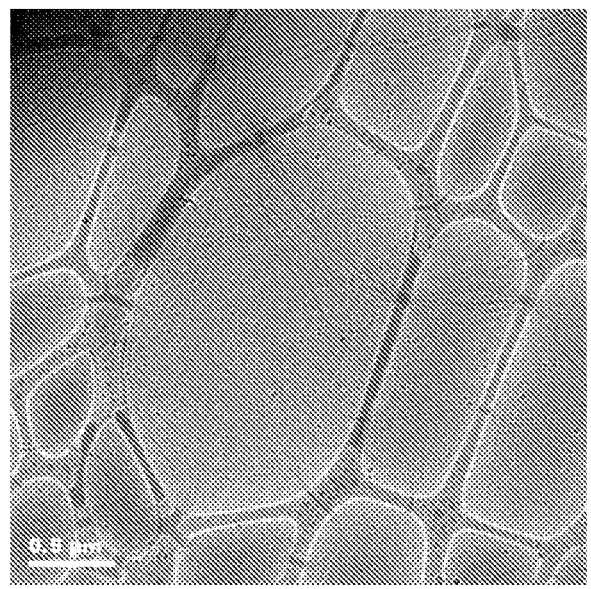
FIG. 3. Cryo transmission electron microscopy (cryoTEM) of fibrils formed from water/dichloromethane emulsion solvent evaporation of $PEG_{44}$-$OES_3$.

PEG-OES as prepared in Example 1 was dissolved in low vapor pressure organic solvent, here chosen as dichloromethane. After dropwise addition of water, the resulting emulsion was allowed to stir at room temperature until complete evaporation of organic solvent, resulting in high-aspect-ratio linear fibrils, as confirmed by cryo transmission electron microscopy (FIG. 3). The resultant fibrils are completely suspendable in aqueous media and solvent exchange through diafiltration achieves fibril suspensions in aqueous media such as phosphate-buffered saline solutions or media. The hydrophobic and crystalline character of the short (DP=3) OES block of PEG-OES drives assembly of the amphiphile into linear fibrillar structures, with a core composed of associated OES chains and PEG blocks radiating outward. OES blocks with DP=4 or higher are expected to generate similar architectures, provided the size of the PEG block provides sufficient solubility to maintain the copolymer in solution during the ring-opening polymerization reaction (no precipitation). In contrast to this finding, in amphiphilic block copolymers composed of PEG and amorphous PPS blocks, a much higher degree of polymerization of propylene sulfide is required to form self-assembled structures. For example, polymerization of propylene sulfide from a $PEG_{44}$ macroinitiator required DP=10 to yield amphiphiles for spherical micelle self-assembly (Velluto et al., 2008). From the same PEG block size, initiation of propylene sulfide polymerization with DP=44 was observed to yield polymers that form cylindrical/fibrillar micelles upon self-assembly, but these structures are metastable and also form spherical micelles (Cerritelli et al., 2009).

Figure 4A:
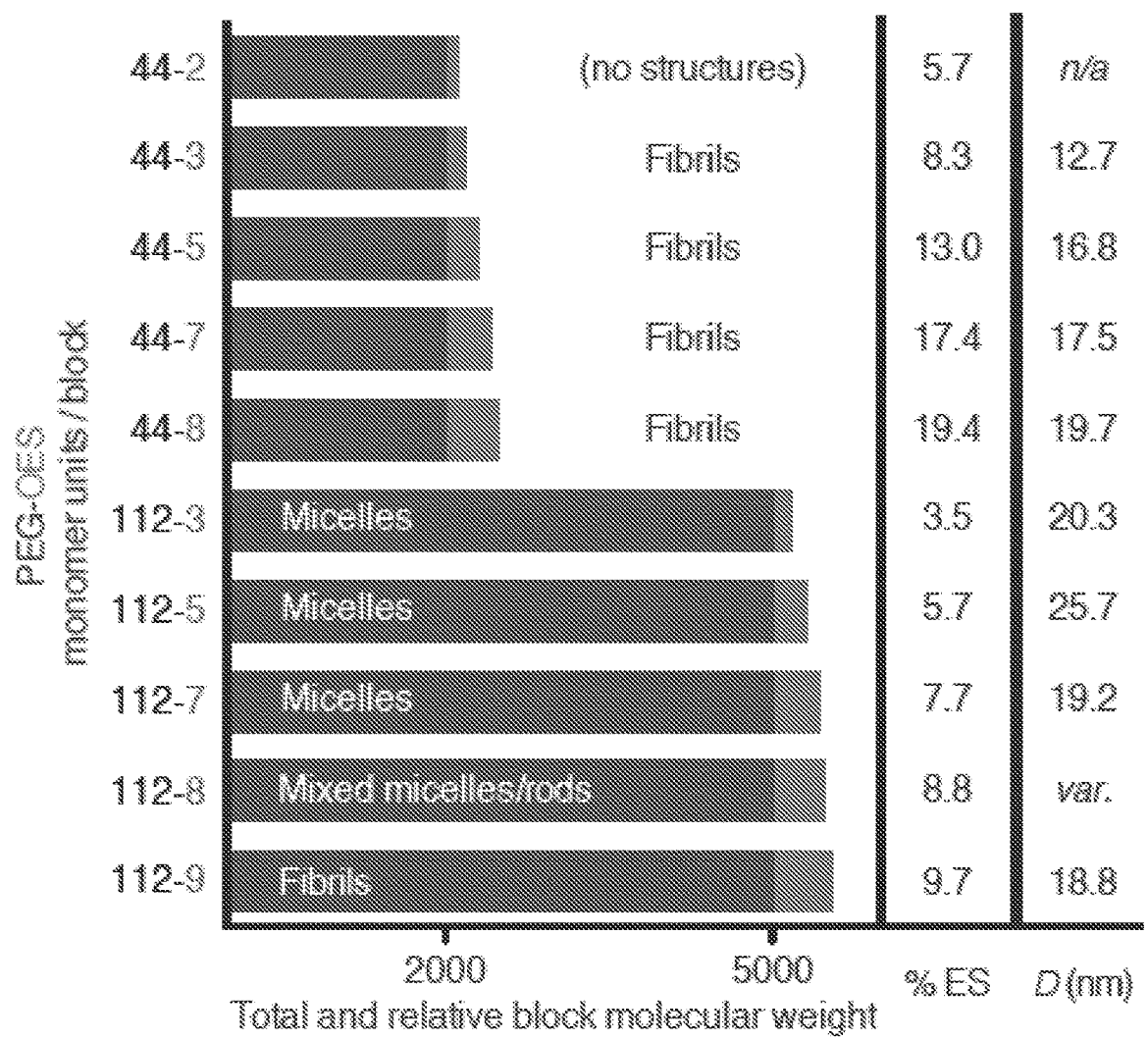
FIG. 4A. Chart showing the relationship between the numbers of monomers and the morphology of the supramolecular assembly. The number n-m indicates the number of ethylene oxide repeating units (n) and the number of ethylene sulfide repeating units (m) in the structure $CH_3(OCH_2CH_2)_nS(CH_2CH_2S)_mH$. % ES designates the weight percentage of the OES block. D(nm) designates the observed assembly diameter; the D value for $PEG_{112}$-$OES_8$ was not obtained because of the variability of the obtained structures.
Figure 4B:
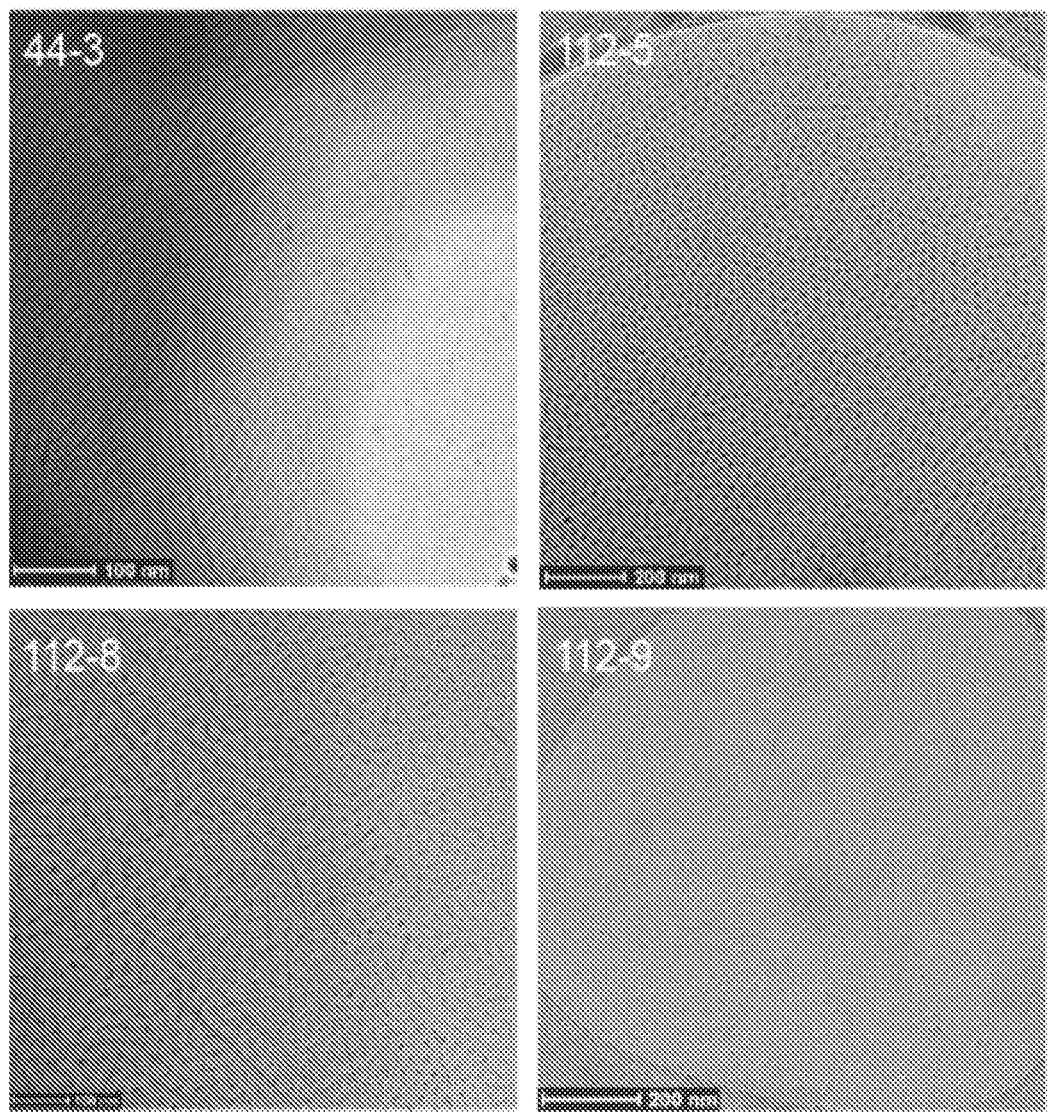
FIG. 4B. CryoTEM images of $PEG_{44}$-$OES_3$ (44-3), $PEG_{112}$-$OES_5$ (112-5), $PEG_{112}$-$OES_8$ (112-8), and $PEG_{112}$-$OES_9$ (112-9).

As shown in FIGS. 4A and 4B, the morphology of supramolecular assemblies of $PEG_n$-$OES_m$ depends on the variables n and m and the resulting molecular weight percentage of the OES block.

Example 5: Incorporation of Linear Fibrils within Polyacrylamide Gel 50 microliters acrylamide and 75 microliters 4× Tris buffer pH 6.8 were mixed. 175 microliters fibril suspension in water (1-10 mg/mL) were added to dilute the mixture and introduce the fibrils. 2.5 microliters of ammonium persulfate solution and 0.5 microliters TEMED reagent were added to initiate gelation of fibril-embedded polyacrylamide matrix. Although a specific hydrogelator is described, the approach may be generalized for linear fibril embedding in the context of cross-linked polymer, polysaccharide, or polypeptide gels.

Example 6: Covalent Modification of Fibril Assembly

Figure 5:
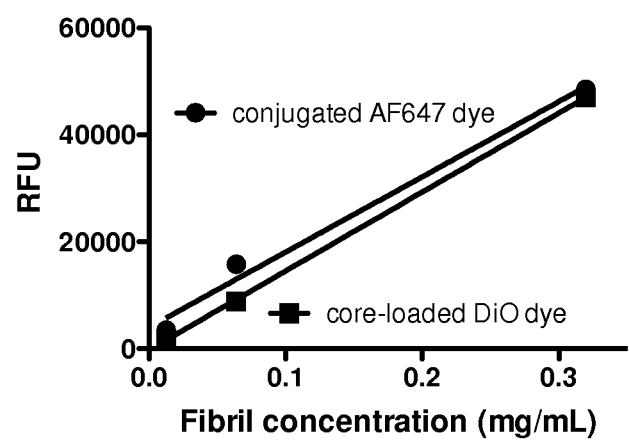
FIG. 5. Fluorescence of conjugated and core-loaded dyes was fibril concentration-dependent and demonstrated two unique methods for molecular modification of fibrils. Each data point represents the mean of samples acquired in triplicate; error bars not visible due to low SEM values.

Linear fibril assembly dispersed in water was incubated overnight at room temperature with a maleimide-conjugated dye, for example Alexa Fluor 647 $C_2$ maleimide (AF647), which reacted with chemically available thiol groups presented from the OES core. Thiol availability was previously confirmed via Ellman's assay. Fibrils covalently modified with fluorescent label were exhaustively dialyzed to remove unreacted label. Fluorescence signature of loaded fibrils was confirmed spectrophotometrically (FIG. 5). Fibril modification with small molecules via reactive thiols represents a general approach; furthermore, the incorporation of chemically-reactive groups at the fibril surface presenting constituent block copolymer PEG termini provides another location to perform single or orthogonal covalent molecular attachment. Larger molecules may be covalently attached in this way to linear or three-dimensional fibril assemblies. The preparation of multivalent fibril structures presenting multiple biologically-relevant compounds is achieved by mixing a heterogeneous population of pre-conjugated and/or reactive constituent polymers, followed by orthogonal loading techniques or sequential deprotection/modification. Such approaches allow the formulation of linear or three-dimensional fibril assemblies presenting complementary biological signals, for example adjuvant and antigen.

Example 7: Non-Covalent Loading of Hydrophobic Small Molecule into Linear Fibril Assembly Linear constituent PEG-OES sulfide block copolymer and lipophilic membrane fluorescent dye (DiO) were dissolved in dichloromethane. Water was added dropwise and the emulsion was stirred at high speed until complete dichloromethane evaporation. The resulting aqueous solution was subjected to exhaustive dialysis to remove unloaded fluorescent label. Fluorescence signature of loaded fibrils was confirmed spectrophotometrically (FIG. 5). This technique represents a broadly applicable technique for loading hydrophobic small molecules into linear or three-dimensional fibril assemblies, that may or may not have covalent modifications as described in Example 8.

Example 8: Hydrogen Peroxide-Mediated Fibril Disassembly

Figure 6A:
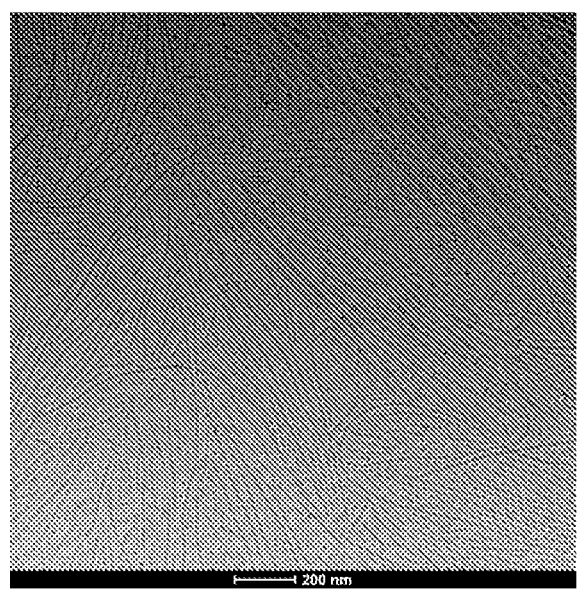
FIG. 6A. Cryo transmission electron microscopy of $PEG_{44}$-$OES_3$ fibrils treated with 1% hydrogen peroxide.
Figure 6B:
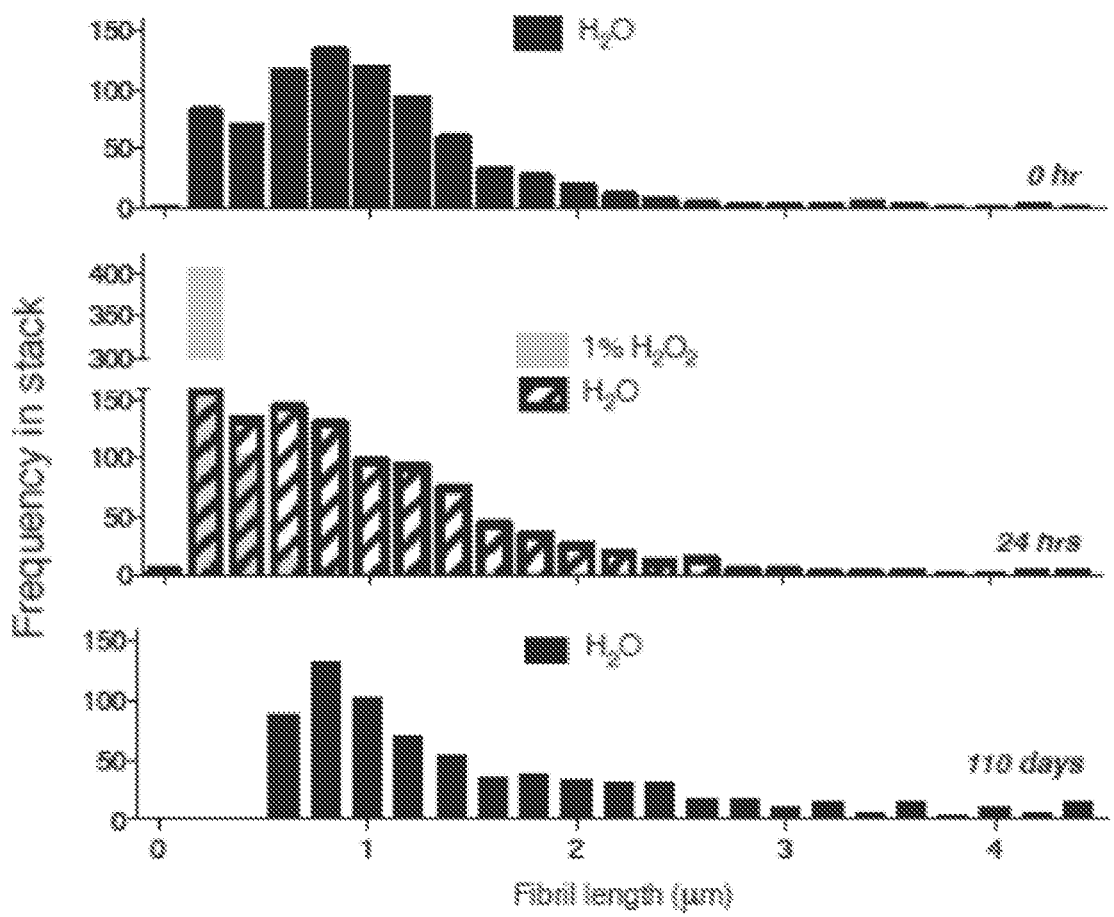
FIG. 6B. Histograms showing that exposure of $PEG_{44}$-$OES_3$ leads to fibril shortening as observed by confocal microscopy.
Figure 7:
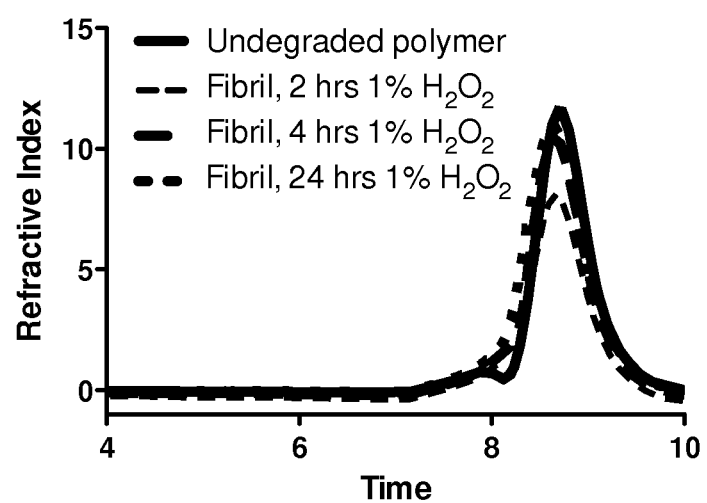
FIG. 7. Ultra high performance liquid chromatography (isocratic flow in dimethylformamide) of fibrils treated with 1% hydrogen peroxide over time.
Figure 8:
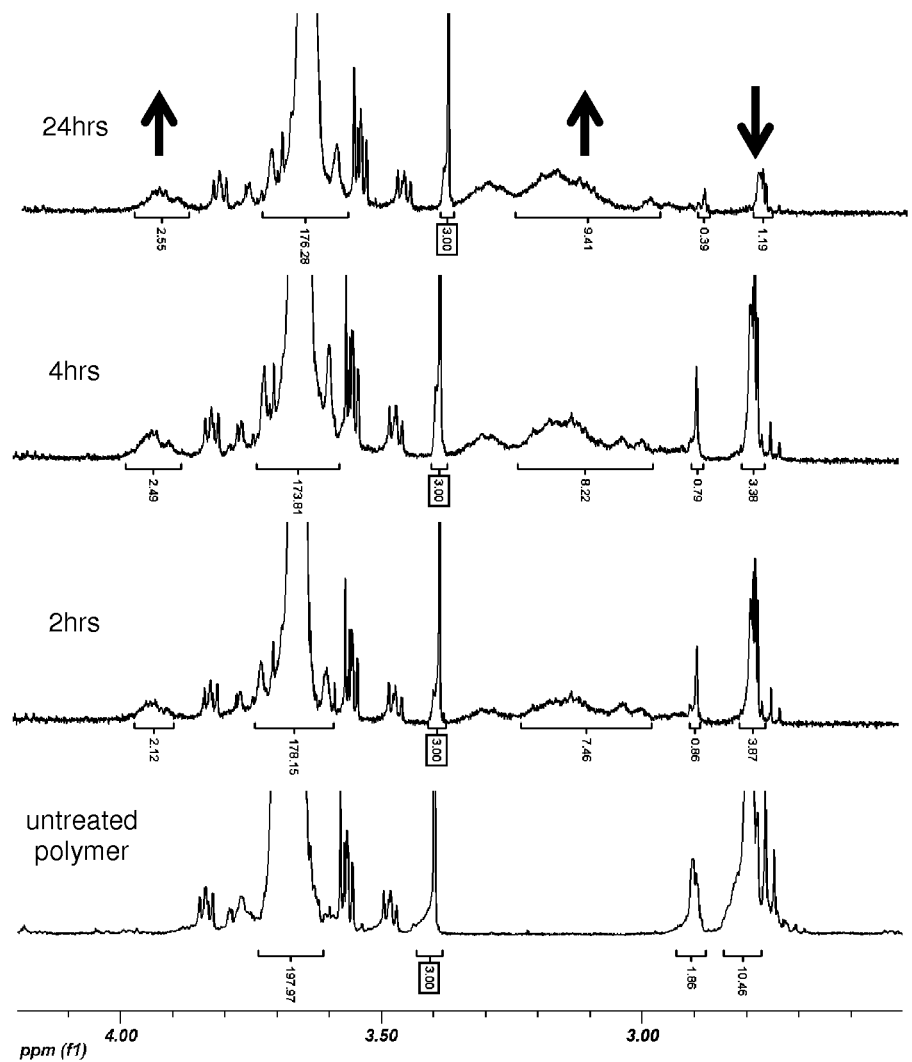
FIG. 8. 1H-NMR of 1% $H_2O_2$-treated $PEG_{44}$-$OES_3$ fibrils and unmodified polymer demonstrated increasing hydrophilic sulfoxide and sulfone signal with time, in parallel with decreasing sulfide signal.

A suspension of linear fibrils was reacted with varying concentrations of hydrogen peroxide for pre-determined periods of time. Cryo transmission electron microscopy (FIG. 6A) performed on unlyophilized, exhaustively diafiltered aqueous fibril solutions confirmed fibril shortening and formation of micellar particles, assemblies whose higher interfacial curvature is favored under such conditions (Napoli et al., 2005). Oxidized polymers were subjected to UHPLC in dimethylformamide under isocratic flow (FIG. 7) and 1H-NMR in chloroform-d (FIG. 8). These techniques confirmed time-dependent conversion of sulfide groups to more hydrophilic sulfoxide and sulfone groups, with no change in relative length of the fibril constituent polymer. Histograms in FIG. 6B demonstrate that exposure of the linear fibrils to 1% hydrogen peroxide leads to fibril shortening, as observed by confocal microscopy. In contrast, no change in fibril length was observed upon long-term storage in water.

Figure 9:
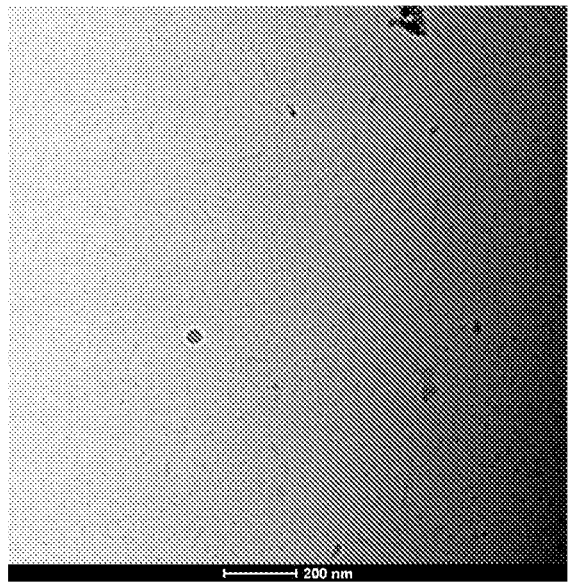
FIG. 9. Cryo transmission electron microscopy of lyophilized, reconstituted fibrils.

Example 9: Linear Fibril Shortening to Rod-Like and Micellar Structures by a Physical Process of Lyophilization Mechanical processing can be utilized to adjust fibril architecture following assembly. An aqueous suspension of previously formed fibrils was flash frozen in liquid nitrogen and lyophilization. Following resuspension in ultrapure water, cryo transmission electron microscopy (FIG. 9) confirmed that this treatment yields rod-like and micellar structures, possibly through shear. This example also confirms that fibril suspensions are preferably not lyophilized prior to downstream applications, as the process changes the desired high aspect ratio shape.

Figure 10A:
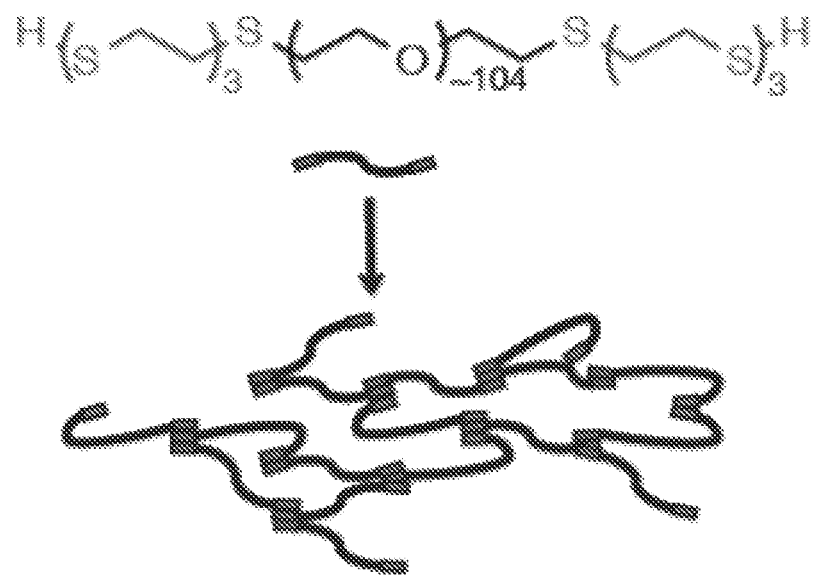
FIG. 10A. Assembly of linear OES-PEG-OES block copolymer into a matrix.
Figure 10B:
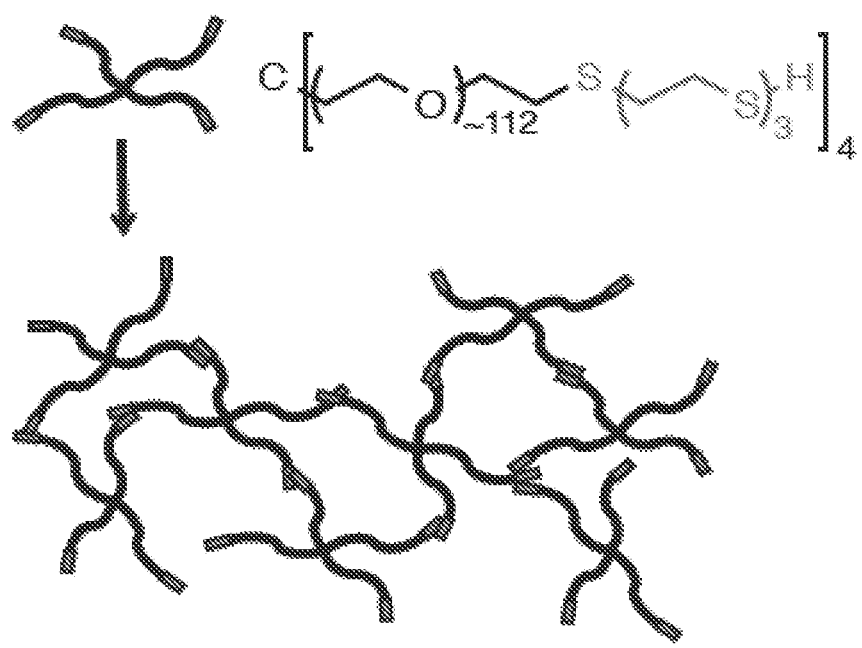
FIG. 10B. Assembly of multiarm C(PEG-OES)$_4$ block copolymer into a matrix.
Figure 11:
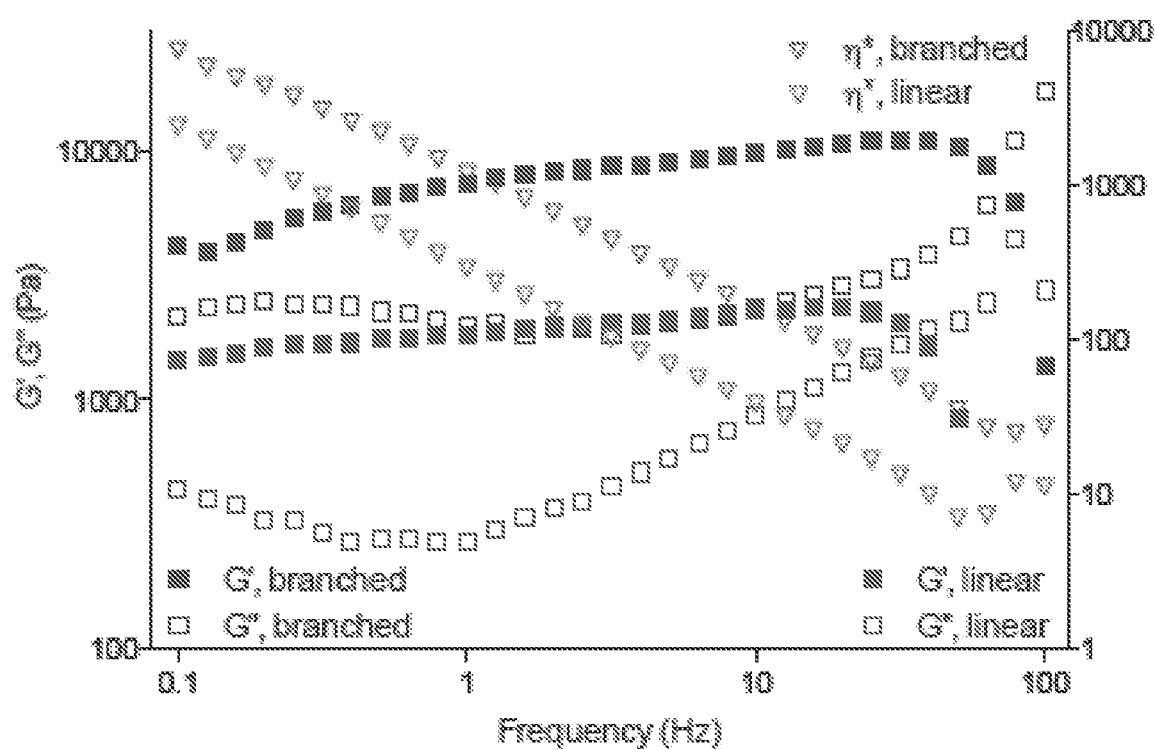
FIG. 11. Graph of the rheological analysis of hydrogel samples composed of linear or multi-arm precursors. G' (closed squares) and G" (open squares) correspond to storage and loss moduli, respectively. η* (open inverted triangles) corresponds to complex viscosity.

Example 10: OES-Terminated Linear and Multi-Arm Polymers form Shear-Thinning Hydrogels As shown in FIGS. 10A and 10B, the OES-terminated linear and multi-arm polymers containing PEG and OES form a matrix. Hydrogels generated from linear and branched precursors are shear-thinning, as demonstrated by frequency-dependent changes in storage (G', closed squares) and loss (G", open squares) moduli (FIG. 11). Inverse linear dependence of complex viscosity (q*, open inverted triangles) on frequency underlines the solid to liquid transition in both systems.

Figure 12:
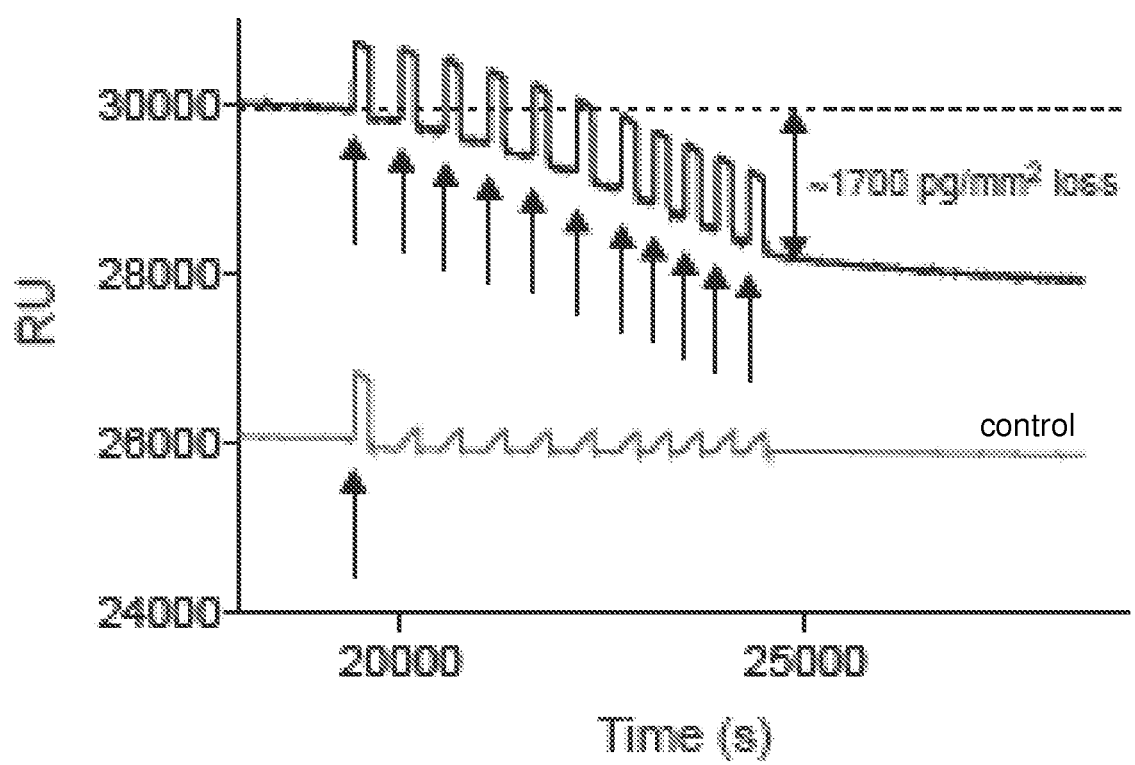
FIG. 12. Graph of the surface plasmon resonance analysis of a hydrogel sample composed of multi-arm precursors. Each one-headed black-arrow indicates exposure of the hydrogel to the mobile phase (1% hydrogen peroxide) for 30 seconds. The control sample was exposed to the mobile phase bursts (water).

FIG. 12 shows surface plasmon resonance analysis oxidation-responsive gel degradation of hydrogel sample composed of branched precursor. In this Example, the hydrogel was exposed to mobile phase or 1% hydrogen peroxide bursts (30 s, single-headed black arrows). Following a single hydrogen peroxide exposure event in the control flow cell (lower trace), no mass loss was observed upon continuous exposure to the mobile phase (water). In contrast, repeated exposure to hydrogen peroxide accumulates mass loss (double-headed black arrow) from hydrogel in the exposure flow cell (upper trace)

Example 11: Aqueous Dispersions of Linear Fibril Assemblies are Phagocytosed In Vitro RAW-Blue mouse macrophages (InvivoGen) were cultured according to vendor instructions. One day prior to visualization, macrophages were plated at 50,000 cells per well in collagen-coated glass-bottom culture trays. Cells were labeled with fluorescent intracellular cytoplasmic stain (for example, CellTracker Red) and incubated with linear AF647-modified fibril-containing media for three hours, then rinsed with fresh media. Nuclear stain (for example, Hoechst 33342) was added to culture wells immediately prior to visualization by spinning disc confocal microscopy. Confocal microscopy confirmed that macrophages phagocytose linear fibril fragments in vitro; in three-dimensional (Z-stack) analysis, the nuclear and cytoplasmic compartments were clearly labeled and delineated, with punctate AF647 fibril signal distributed within the cytoplasmic compartment. These findings support downstream biological applications for fibril-mediated molecular delivery to phagocytic immune cells such as specialized macrophage subsets and dendritic cells.

Example 12: Intradermal Injection of Fibril Suspension for Depot Effect or Molecular Delivery to Downstream Sentinel Lymph Node Mice were intradermally injected under isoflurane anesthesia at each forelimb and hindlimb hock with a suspension of AF647-modified linear fibrils, as prepared in Example 6. The total amount of injected fibril was 100 µg per mouse, with or without 10 µg soluble Toll-like receptor ligand CpG-B. One vehicle mouse received sterile Dulbecco's phosphate buffered saline alone. Relevant secondary lymphoid organs were harvested 24 hr later and processed for flow cytometry to assess fibril distribution and cellular association following intradermal injection, in the absence or presence of CpG-B-mediated inflammation. In both cases, fibril-positive signal was comparable to background (vehicle) in the spleen, indicating that intact or phagocytosed fibrils did not reach the spleen over the period of one day (FIG. 13A).

Figure 13:
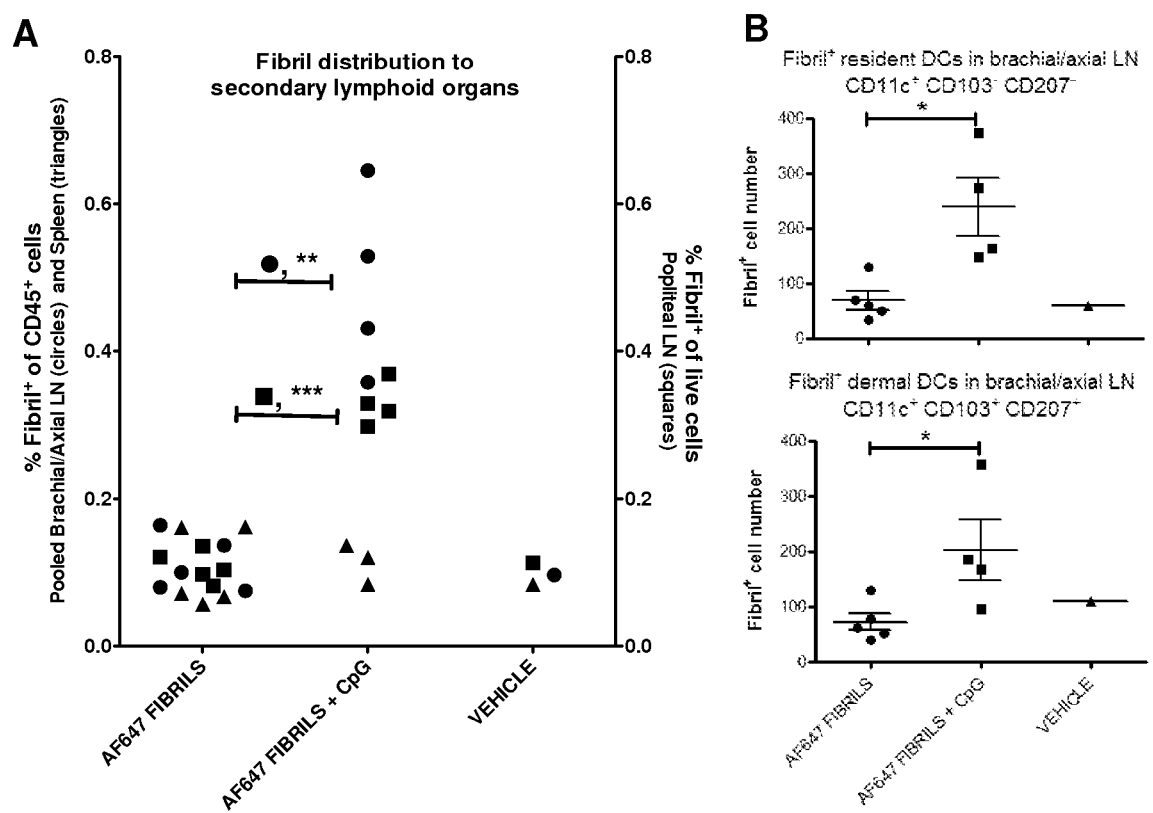
FIG. 13. Fibril distribution to selected subsets in secondary lymphoid organs after intradermal injection.

In the context of fibril injection without CpG-B, fibril-positive signal was comparable to background (vehicle) in the downstream sentinel lymph nodes, whether pooled axial and brachial lymph nodes associated with the forelimb injection sites, or popliteal lymph nodes associated with the hindlimb injection sites (FIG. 13A). This finding suggests that the majority of injected fibril suspension remained at the injection site. As such, intradermally injected suspensions of fibrils bearing covalently- or non-covalently-bound biomolecules or small molecule drugs could be utilized for depot effect at the injection site. Similar depot effects may also be achieved by subcutaneous implantation of matrix-like three-dimensional fibril constructs.

In the context of fibril injection with CpG-B, fibril-positive signal in CD45-positive cells (brachial/axial lymph nodes) or all live cells (popliteal lymph nodes) was significantly greater than background. This finding suggests that in the context of local inflammation, intact or phagocytosed fibril was transported to the sentinel lymph node. For example, in brachial/axial lymph nodes, cell counts of fibril-positive lymph node-resident dendritic cells and peripheral dendritic cells showed that both populations were increased in the context of CpG-B (FIG. 13B). This result indicates that under such conditions, fibril transport to the sentinel lymph node was both flow- and cell-mediated. This approach may be applied for fibril-mediated delivery of biomolecules to antigen-presenting cells or for delivery of immunomodulatory drugs to the lymph node.

Example 13: Drug and Small Molecule Delivery to Tumor

Figure 14:
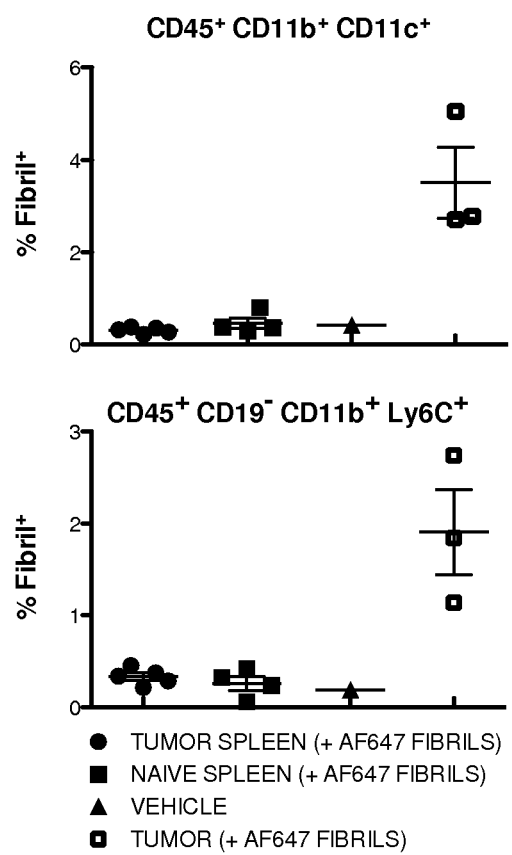
FIG. 14. Fibril associated with tumor-resident immune cell subsets following intravenous injection.

Intravenous injection of fibril suspensions was explored in the context of tumor-bearing and naïve mice. Tumor-bearing mice previously received subcutaneous cultured GFP B16F10 mouse melanoma xenotransplant at the left shoulder blade; tumors were monitored daily for one week prior to fibril injection. Tumor-bearing and naïve mice received 100 µg total fibril in 100 µL volume per mouse, while vehicle mouse received Dulbecco's phosphate-buffered saline. After 3 hr, tumors from tumor-bearing mice, as well as spleens from tumor-bearing, naive, and vehicle mice were harvested for flow cytometry, to assess fibril distribution and cellular association following intravenous injection. In both tumor-bearing and naive mice, fibril signal in spleen was comparable to background (vehicle), while signal was significantly associated with tumor-associated $CD11b^+$ $CD11c^+$ populations (dendritic cells and some macrophage populations; FIG. 14, top panel). Within tumor, fibril signal also associated with the monocytic phenotype of myeloid-derived suppressor cells (FIG. 14, bottom panel). As they show that fibrils associated with the tumor mass and with tumor-related immune cell subsets, these findings support the exploration of anti-tumor drug and/or small molecule delivery to tumor, for potential therapeutic applications.

Example 14: T Cell-Dependent and -Independent Vaccine Technology

Figure 15:
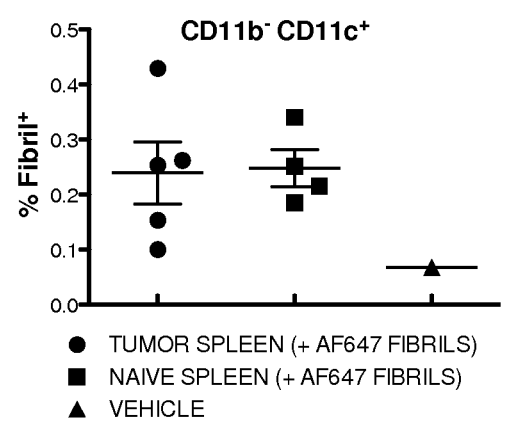
FIG. 15. Fibril associated with splenic dendritic cells following intravenous injection independent of tumor burden.

In the context of the intravenous fibril administration route introduced in Example 13, we observed that fibril association varied by tissue type and immune cell subset. For example, a small but notable population of CD11b– CD11c+ dendritic cells were fibril positive in the splenic compartment, independent of tumor burden (FIG. 15). This outcome suggests that following IV injection a portion of the fibril bolus was taken up in the spleen, a lymphoid organ highly relevant for lymphocyte immune response to circulating antigens. In particular, fibril covalently conjugated with peptide or protein antigens could be utilized for T cell-mediated humoral response to loaded antigen, and fibril covalently conjugated with repetitive structures for clustered B cell receptor engagement could be utilized for T cell-independent humoral response. Both of these approaches represent directions for use of linear fibril suspensions for vaccine technology.

REFERENCES

Cerritelli, S., O'Neil, C. P., Velluto, D., Fontana, A., Adrian, M., Dubochet, J., and Hubbell, J. A. (2009). Aggregation behavior of poly(ethylene glycol-bl-propylene sulfide) di- and triblock copolymers in aqueous solution. Langmuir 25, 11328-11335.

Cerritelli, S., Velluto, D., and Hubbell, J. A. (2007). PEG-SS-PPS: Reduction-sensitive disulfide block copolymer vesicles for intracellular drug delivery. Biomacromolecules 8, 1966-1972.

Geng, Y., Dalhaimer, P., Cai, S., Tsai, R., Tewari, M., Minko, T., and Discher, D. E. (2007). Shape effects of filaments versus spherical particles in flow and drug delivery. Nat Nanotechnol 2, 249-255.

Geng, Y., and Discher, D. E. (2005). Hydrolytic degradation of poly(ethylene oxide)-block-polycaprolactone worm micelles. J Am Chem Soc 127, 12780-12781.

Han, P., Ma, N., Ren, H., Xu, H., Li, Z., Wang, Z., and Zhang, X. (2010). Oxidation-responsive micelles based on a selenium-containing polymeric superamphiphile. Langmuir 26, 14414-14418.

Hartgerink, J. D., Beniash, E., and Stupp, S. I. (2001). Self-assembly and mineralization of peptide-amphiphile nanofibers. Science 294, 1684-1688.

Jo, Y. S., van der Vlies, A. J., Gantz, J., Antonijevic, S., Demurtas, D., Velluto, D., and Hubbell, J. A. (2008). RAFT homo- and copolymerization of N-acryloyl-morpholine, piperidine, and azocane and their self-assembled structures. Macromolecules 41, 1140-1150.

Kouwer, P. H., Koepf, M., Le Sage, V. A., Jaspers, M., van Buul, A. M., Eksteen-Akeroyd, Z. H., Woltinge, T., Schwartz, E., Kitto, H. J., Hoogenboom, R., Picken, S. J., Nolte, R. J., Mendes, E., and Rowan, A. E. (2013). Responsive biomimetic networks from polyisocyanopeptide hydrogels. Nature 493, 651-655.

Mahmoud, E. A., Sankaranarayanan, J., Morachis, J. M., Kim, G., and Almutairi, A. (2011). Inflammation responsive logic gate nanoparticles for the delivery of proteins. Bioconj Chem 22, 1416-1421.

Napoli, A., Bermudez, H., and Hubbell, J. A. (2005). Interfacial reactivity of block copolymers: Understanding the amphiphile-to-hydrophile transition. Langmuir 21, 9149-9153.

Napoli, A., Tirelli, N., Kilcher, G., and Hubbell, J. A. (2001). New synthetic methodologies for amphiphilic multiblock copolymers of ethylene glycol and propylene sulfide. Macromolecules 34, 8913-8917.

Napoli, A., Valentini, M., Tirelli, N., Muller, M., and Hubbell, J. A. (2004). Oxidation-responsive polymeric vesicles. Nat Mater 3, 183-189.

Rudra, J. S., Tian, Y. F., Jung, J. P., and Collier, J. H. (2010). A self-assembling peptide acting as an immune adjuvant. Proc Natl Acad Sci USA 107, 622-627.

Segura, T., and Hubbell, J. A. (2007). Synthesis and in vitro characterization of an ABC triblock copolymer for siRNA delivery. Bioconj Chem 18, 736-745.

Silva, G. A., Czeisler, C., Niece, K. L., Beniash, E., Harrington, D. A., Kessler, J. A., and Stupp, S. I. (2004). Selective differentiation of neural progenitor cells by high-epitope density nanofibers. Science 303, 1352-1355.

Tarasov, S. G., Gaponenko, V., Howard, O. M., Chen, Y., Oppenheim, J. J., Dyba, M. A., Subramaniam, S., Lee, Y., Michejda, C., and Tarasov, N. I. (2011). Structural plasticity of a transmembrane peptide allows self-assembly into biologically active nanoparticles. Proc Natl Acad Sci USA 108, 9798-9803.

Vasdekis, A. E., Scott, E. A., O'Neil, C. P., Psaltis, D., and Hubbell, J. A. (2012). Precision intracellular delivery based on optofluidic polymersome rupture. ACS Nano 6, 7850-7857.

Velluto, D., Demurtas, D., and Hubbell, J. A. (2008). PEG-b-PPS diblock copolymer aggregates for hydrophobic drug solubilization and release: Cyclosporin A as an example. Mol Pharm 5, 632-642.

Webber, M. J., Matson, J. B., Tamboli, V. K., and Stupp, S. I. (2012). Controlled release of dexamethasone from peptide nanofiber gels to modulate inflammatory response. Biomaterials 33, 6823-6832.

Wilson, D. S., Dalmasso, G., Wang, L., Sitaraman, S. V., Merlin, D., and Murthy, N. (2010). Orally delivered thioketal nanoparticles loaded with TNF-alpha-siRNA target inflammation and inhibit gene expression in the intestines. Nat Mater 9, 923-928.

Other Embodiments

Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A block copolymer comprising a single hydrophilic block, a single oligo(ethylene sulfide) (OES) block, and a moiety; wherein the moiety is a fluorophore; a peptide; a chemokine; a Toll-like receptor ligand; a pathogen-associated molecular pattern (PAMP); a damage-associated molecular pattern (DAMP); a natural protein; a recombinant protein; a protein conjugate; a sugar; a saccharide; or a synthetic polymer; wherein the moiety is covalently attached to the OES block.

2. The block copolymer of claim 1, wherein the hydrophilic block is selected from the group consisting of a poly(ethylene oxide)-co-poly(propylene oxide) random copolymer, a poly(ethylene oxide)-co-poly(propylene oxide) diblock copolymer, a poly(ethylene oxide)-co-poly(propylene oxide) multiblock copolymer, poly(ethylene oxide), poly(vinyl alcohol), poly(ethylene-co-vinyl alcohol), poly(N-vinyl pyrrolidone), poly(acrylic acid), poly(methyloxazoline), poly(ethyloxazoline), poly(alkylacrylates), poly(acrylamide), poly(N-alkylacrylamides), polypeptide, polysaccharide, poly(N,N-dialkylacrylamides), hyaluronic acid, alginate, cyclodextrin, and poly (N-acryloylmorpholine).

3. The block copolymer of claim 1, wherein the hydrophilic block is poly(ethylene oxide).

4. The block copolymer of claim 3, wherein the poly(ethylene oxide) is of molecular weight 500 to 50,000.

5. The block copolymer of claim 1, wherein the degree of polymerization of the OES block is 2 to 10.

6. The block copolymer of claim 1, wherein the block copolymer is linear.

7. A supramolecular assembly comprising a plurality of block copolymers of claim 1.

8. The supramolecular assembly of claim 7, wherein the assembly is a fibril, rod, micelle, or matrix.

9. The supramolecular assembly of claim 7, wherein the plurality of block copolymers comprises linear copolymers self-assembled or covalently linked to form the matrix.

10. The supramolecular assembly of claim 7, further comprising a second polymer matrix.

11. The supramolecular assembly of claim 10, wherein the second polymer matrix forms a polymer interpenetrating network with the plurality of block copolymers.

12. The supramolecular assembly of claim 10, wherein the block copolymers form fibrils that are dispersed in the second polymer matrix.

13. The supramolecular assembly of claim 7, further comprising a hydrophobic or amphoteric molecule dissolved or dispersed in the assembly.

14. The supramolecular assembly of claim 13, wherein the hydrophobic or amphoteric molecule is selected from the group consisting of a fluorophore; peptide; chemokine; a Toll-like receptor ligand; a pathogen-associated molecular pattern (PAMP); a damage-associated molecular pattern (DAMP); and conjugates thereof.

15. A method of delivering a target molecule to a subject, the method comprising providing a supramolecular assembly of claim 7, wherein the supramolecular assembly comprises the target molecule; contacting the subject with the supramolecular assembly, thereby delivering the target molecule to the subject.

16. The method of claim 15, wherein the target molecule
   is covalently attached to the supramolecular assembly; or
   is a hydrophobic molecule dissolved or dispersed in the supramolecular assembly.

17. The method of claim 15, wherein the supramolecular assembly
   is a depot deposited internally in the subject; or
   is dispersed in a liquid carrier when contacted with the subject.

18. A pharmaceutical composition comprising the supramolecular assembly of claim 7 and a pharmaceutically acceptable carrier.

* * * * *